US011952583B2

(12) United States Patent
Vriezen

(10) Patent No.: US 11,952,583 B2
(45) Date of Patent: Apr. 9, 2024

(54) DOWNY MILDEW RESISTANT LETTUCE MUTANT

(71) Applicant: NUNHEMS B.V., Nunhem (NL)

(72) Inventor: Wim Vriezen, Nunhem (NL)

(73) Assignee: Nunhems B.V., Nunhems (NL)

( * ) Notice: Subject to any disclaimer, the term of this patent is extended or adjusted under 35 U.S.C. 154(b) by 42 days.

(21) Appl. No.: 17/283,877

(22) PCT Filed: Sep. 19, 2019

(86) PCT No.: PCT/EP2019/075263
§ 371 (c)(1),
(2) Date: Apr. 8, 2021

(87) PCT Pub. No.: WO2020/074237
PCT Pub. Date: Apr. 16, 2020

(65) Prior Publication Data

US 2021/0348187 A1 Nov. 11, 2021

(30) Foreign Application Priority Data

Oct. 11, 2018 (EP) .................................... 18199989

(51) Int. Cl.
*C12N 15/82* (2006.01)
*C12N 9/12* (2006.01)

(52) U.S. Cl.
CPC ....... *C12N 15/8279* (2013.01); *C12N 9/1205* (2013.01); *C12Y 207/01039* (2013.01)

(58) Field of Classification Search
None
See application file for complete search history.

(56) References Cited

U.S. PATENT DOCUMENTS 8,237,019 B2 * 8/2012 Van Den Ackerveken ................. C12N 15/8279 800/278

FOREIGN PATENT DOCUMENTS

| | | | |
|---|---|---|---|
| EP | 28011 | B1 | 11/1986 |
| EP | 1957655 | B1 | 8/2016 |
| WO | 70016 | A2 | 11/2000 |
| WO | 02088301 | A2 | 11/2002 |
| WO | 2005124108 | A2 | 12/2005 |
| WO | 2007/051626 | A2 | 5/2007 |
| WO | 2007051483 | A1 | 5/2007 |
| WO | 2015/193418 | A1 | 12/2015 |
| WO | 2020239186 | A1 | 12/2020 |
| WO | 2022048726 | A1 | 3/2022 |

OTHER PUBLICATIONS

EBI Database Accession No. A0A2J6LHE4, https://www.uniprot.org/uniprot/A0A2J6LHE4.txt, May 23, 2018, 1 page.

Eenink, et al., "Resistance of Lettuce (*Lactuca*) to the leaf aphid *Nasonovia ribis* nigri. 1. Transfer of resistance from L. virosa to *L. sativa* by interspecific crosses and selection of resistant breeding lines", Euphytica, vol. 31, Issue 2, Sep. 1982, pp. 291-299.

European Search Report for EP Patent Application No. 18199989.7, dated Mar. 19, 2019, 4 pages.

Henikoff, et al., "Amino acid substitution matrices from protein blocks", Proceedings of the National Academy of Sciences of the United States of America, vol. 89, Issue 22, Nov. 15, 1992, pp. 10915-10919.

Maisonneuve, et al., "Sexual and somatic hybridization in the genus *Lactuca*", Euphytica, vol. 85, Issue 1, Feb. 1995, pp. 281-285.

Maisonneuve, et al., "Utilisation de la culture in vitro d'embryons immatures pour les croisements interspécifiques entre *Latuca sativa* L. et L. saligha L. ou L. virosa L. ; étude des hybrides obtenus", Agronomie, vol. 7, Issue 5, 1987, pp. 313-319.

Teng, et al., "Rapid regeneration of lettuce from suspension culture", HortScience, vol. 27, Issue 9, Sep. 1, 1992, pp. 1030-1032.

Teng, et al., "Regenerating lettuce from suspension culture in a 2-Liter bioreactor", HortScience, vol. 28, Issue 6, Jun. 1, 1993, pp. 669-671.

Van Damme, et al., "Downy Mildrew Resistance in *Arabidopsis* by Mutation of Homoserine Kinase", The Plant Cell, vol. 21, Issue 7, Jul. 21, 2009, pp. 2179-2189.

Van Damme, et al., "Identification of *Arabidopsis* loci required for susceptibility to the downy mildew pathogen Hyaloperonospora parasitica", Molecular Plant-Microbe Interations, vol. 18, Issue 6, Jun. 2005, pp. 583-592.

Xinrun, et al., "Genotypic effects on tissue culture response of lettuce cotyledons", Journal of Genetics and Breeding, vol. 46, Issue 3, 1992, pp. 287-290.

Zeilmaker et al., "Arabidopsis Homoserine Kinase Tilling mutants; engineering resistance to downy mildew by mutation," In: Functional and applied aspects of the Downy Mildew Resistant 1 and 6 genes in Arabidopsis, Chapter 3, 1980, pp. 55-72.

Zeilmaker, T., "Functional and applied aspects of the Downy Mildew Resistant 1 and 6 genes in Arabidopsis," PhD Thesis, University of Utrecht, Feb. 6, 2012, 147 pages.

Zhang et al., "Three Combined Quantitative Trait Loci from Nonhost Lactuca saligna Are Sufficient to Provide Complete Resistance of Lettuce Against *Bremia lactucae*," Molecular Plant-Microbe Interactions, 2009, vol. 22, No. 9, pp. 1160-1168.

International Search Report dated Apr. 27, 2007 in PCT/EP2006/010535, 3 pages.

Adjustments on the Agilent UHPLC instructions of use for L-homoserine measurements, filed in Opposition of EP Patent No. EP1957655, Jan. 8, 2018, 2 pages.

Agilent ZORBAX Eclipse AAA Instructions for Use, Jun. 13, 2008, 2 pages.

Annex with Experimental Evidence, filed in Opposition of EP Patent No. EP1957655, Oct. 11, 2018, 10 pages.

Appendix A: Silencing of homoserine kinase (DMR1) in lettuce variety Pinokkio, filed in Opposition of EP Patent No. EP1957655, Jan. 8, 2018, 2 pages.

(Continued)

*Primary Examiner* — Medina A Ibrahim
(74) *Attorney, Agent, or Firm* — ArentFox Schiff LLP

(57) ABSTRACT

The invention relates to lettuce plants comprising in its genome a mutant homoserine kinase allele in homozygous form, whereby the plants are resistant against *Bremia lactucae*.

13 Claims, 2 Drawing Sheets

Specification includes a Sequence Listing.

(56) References Cited

OTHER PUBLICATIONS

Arabidopsis thaliana homoserine kinase (HSK) mRNA, complete cds, Database Accession No. AF082525, Feb. 29, 2000, 2 pages.
Aubert et al. "Transport, Compartmentation, and Metabolism of Homoserine in Higher Plant Cells: Carbon-13- and Phosphorus-31-Nuclear Magnetic Resonance Studies," Plant Physiology, 1998, vol. 116, No. 2, pp. 547-557.
Azevedo et al., "The Biosynthesis and Metabolism of the Aspartate Derived Amino Acids in Higher Plants," Phytochemistry, 1997, vol. 46, No. 3, pp. 395-419.
Brewer et al., "Mutations in the Arabidopsis homoserine kinase gene DMR1 confer enhanced resistance to Fusarium culmorum and F. graminearum," BMC Plant Biology, 2014, vol. 14, No. 317, 15 pages.
Commission Notice on certain articles of Directive 98/44/EC of the European Parliament and of the Council on the legal protection of biotechnological inventions, Official Journal of the European Union, 2016, pp. C411/3-C411/14.
Constantinescu et al., "Peronospora-like fungi (Chromista, Peronosporales) parasitic on Brassicaceae and related hosts," Nova Hedwigia, 2002, vol. 74, No. 3-4, pp. 291-338.
Dai et al., "Involvement of phenolic compounds in the resistance of grapevine callus to downy mildew (Plasmopara viticola)," European Journal of Plant Pathology, 1995, vol. 101, pp. 541-547.
Declaration, Dr. ir. Karin Ingeborg Posthuma, filed in Opposition of EP Patent No. EP1957655, Oct. 31, 2013, 3 pages.
Declaration, Dr. Tieme Zeilmaker, including Exhibits A-D, filed in Opposition of EP Patent No. EP1957655, May 10, 2022, 35 pages.
Declaration, Mathieu Pel—expert in charge of carrying out the experiments reported in Exhibits D41 and D45A-C, filed in Opposition of EP Patent No. EP1957655, Jan. 4, 2018, 1 page.
Develey-Riviere et al., "Resistance to pathogens and host developmental stage: a multifaceted relationship within the plant kingdom," New Phytologist, 2007, vol. 175, pp. 405-416.
Experimental Evidence, filed in Opposition of EP Patent No. EP1957655, May 5, 2022, 5 pages.
Flanagan et al., "Using SIFT and PolyPhen to Predict Loss-of-Function and Gain-of-Function Mutations," Genetic Testing and Molecular Biomarkers, 2010, vol. 14, No. 4, pp. 533-537.
Geneseq AC AAG451451, Arabidopsis thaliana protein fragment SEQ ID NO. 56649, Oct. 2000.
Goker et al., "Phylogeny of Hyaloperonospora based on nuclear ribosomal internal transcribed spacer sequences," Mycological Progress, May 2004, vol. 3, No. 2, pp. 83-94.
Goker et al., "Taxonomic aspects of Peronosporaceae inferred from Bayesian molecular phylogenetics," Canadian Journal of Botany, 2003, vol. 81, pp. 672-683.
Hong et al., "First confirmed report of downy mildew caused by Hyaloperonospora parasitica on broccoli in Korea," Plant Pathology, 2008, vol. 57, p. 777.
HSK amino acid sequence alignments, filed in Opposition of EP Patent No. EP1957655, May 22, 2017, 4 pages.
Huibers et al., "Powdery Mildew Resistance in Tomato by Impairment of SlPMR4 and SlDMR1," PLoS One, Jun. 2013, vol. 8, No. 6, 8 pages.
Interlocutory Decision on EP 2 455 473 B1, European Patent Office, Dec. 19, 2017, 15 pages.
Jeffrey, C., "A review of the Cucurbitaceae," Botanical Journal of the Linnean Society, Oct. 1980, vol. 81, pp. 233-247.
Lee et al., "Identification of the Gene Encoding Homoserine Kinase from Arabidopsis thaliana and Characterization of the Recombinant Enzyme Derived from the Gene," Archives of Biochemistry and Biophysics, Dec. 1, 1999, vol. 372, No. 1, pp. 135-142.
Lee et al., "Methionine and threonine synthesis are limited by homoserine availability and not the activity of homoserine kinase in Arabidopsis thaliana," The Plant Journal, 2005, vol. 41, pp. 685-696.
Lettuce DMR1 Enza data, Nov. 2017, filed in Opposition of EP Patent No. EP1957655, 4 pages.
Maimann et al., "Transgenic potato plants reveal the indispensable role of cystathionine ß-lysase in plant growth and development," The Plant Journal, 2000, vol. 23, No. 6, pp. 747-758.
Melon DMR1 Enza data, Nov. 2017, filed in Opposition of EP Patent No. EP1957655, 4 pages.
Menda et al., "In silico screening of a saturated mutation library of tomato," The Plant Journal, 2004, vol. 38, pp. 861-872.
Multiple alignment of DMRI from Arabidopsis, onion, melon and lettuce, filed in Opposition of EP Patent No. EP1957655, Jan. 8, 2018, 1 page.
Onion DMR1 Enza data, Nov. 2017, filed in Opposition of EP Patent No. EP1957655, 4 pages.
Pacific Pests and Pathogens Fact Sheet, Cabbage downy mildew (192), Retrieved on Sep. 20, 2017. Retrieved from the Internet <URL:http://www.pestnet.org/fact_sheets/cabbage_downy_mildew_192.htm>, 4 pages.
PCT/EP2005/011718, filed Nov. 1, 2005, Certified Copy of Priority Document, 38 pages.
Rijk Zwaan Report on HSK Mutants in Cucumber, filed in Opposition of EP Patent No. EP1957655, May 22, 2017, 1 page.
Rijk Zwaan Report on HSK Mutants in Spinach, filed in Opposition of EP Patent No. EP1957655, May 22, 2017, 1 page.
Schlegel, R.H.J., Encyclopedic Dictionary of Plant Breeding and Related Subjects, 2003, Haworth Press Inc., Binghamton, New York, pp. 235-236.
Sedlarova et al., "Histochemical Detection and Role of Phenolic Compounds in the Defense Response of *Lactuca* spp. to Lettuce Downy Mildew (*Bremia lactucae*)," Journal of Phytopathology, 2001, vol. 149, pp. 693-697.
Sim et al., "SIFT web server: predicting effects of amino acid substitutions on proteins," Nucleic Acids Research, 2012, vol. 40, pp. W452-W457.
Smart et al., "Best Control of Downy Mildew in Cole Crops," Dept of Plant Pathology and Plant-Microbe Biology, Cornell University, Geneva, NY, 2 pages.
Smart et al., "Identification of quantitative resistance in Lycopersicon pennellii to Phytophthora infestans," filed in Opposition of EP Patent No. EP1957655, Jan. 8, 2018, Phytopathology, vol. 92, No. 6, p. S77.
Stuttmann et al., "Perturbation of Arabidopsis Amino Acid Metabolism Causes Incompatibility with the Adapted Biotrophic Pathogen Hyaloperonospora arabidopsidis," The Plant Cell, Jul. 2011, vol. 23, pp. 2788-2803.
Thines et al., "Taxonomy and Phylogeny of the Downy Mildews," In: Lamour et al. (Eds.), Oomycete Genetics and Genomics: Diversity, Interactions, and Research Tools, John Wiley & Sons, Hoboken, New Jersey, 2008, pp. 52-55.
Thukral et al., "Biochemical genetic basis of downy mildew resistance in pearl millet," Theoretical and Applied Genetics, 1986, vol. 71, pp. 648-651.
Van Damme, M., "Genetic analysis of disease susceptibility in the Arabidopsis-Hyaloperonospora parasitica interaction," PhD Thesis, University of Utrecht, May 27, 2007, 134 pages.
Voglmayr, H., "Phylogenetic relationships of Peronospora and related genera based on nuclear ribosomal ITS sequences," Mycological Research, Oct. 2003, vol. 107, No. 10, pp. 1132-1142.
Wikipedia, "Enzyme assay," dated as recieved May 22, 2017, 6 pages.
Wikipedia, "Hyaloperonospora brassicae," retrieved on Sep. 20, 2017. Retrieved from the Internet <URL:https://en.wikipedia.org/wiki/Hyaloperonospora_brassicae>, 2 pages.
Wikipedia, "Hyaloperonospora parasitica," retrieved on Sep. 20, 2017. Retrieved from the Internet <URL:https://en.wikipedia.org/wiki/Hyaloperonospora_parasitica>, 4 pages.
EBI Database Accession No. JI586151, https://ibis.internal.epo.org/exam/dbfetch.jsp?id=EM_TSA:JI586151, Apr. 25, 2011, 1 page.
EBI Database Accession No. ADA2J6LHE4, https://www.uniprot.org/uniprot/A0A2J6LHE4.txt, May 23, 2018, 1 page.
EBI Database Accession No. A0A2J6M5X6, https://www.uniprot/A0A2J6M5X6.txt, Mar. 28, 2018, 1 page.
Reyes-Chin-Wo, et al., "Genome Assembly with in Vitro Proximity Ligation Data and Whole-genome Triplication in Lettuce," Nature Communications, vol. 8, Apr. 2017, pp. 1-11.

(56) References Cited

OTHER PUBLICATIONS

Sun, et al., "Silencing of Six Susceptibility Genes Results in Potato Late Blight Resistance," Transgenic Res., vol. 25, No. 5, May 2016, pp. 731-742.
International Search Report issued in PCT/EP2019/075263 dated Dec. 11, 2019, pp. 1-5.

* cited by examiner

Figure 1

```
Aligned_sequences: 2
# 1: SEQ ID NO: 1
# 2: SEQ ID NO: 3
# Matrix: EBLOSUM62
# Gap_penalty: 10.0
# Extend_penalty: 0.5
#
# Length: 376
# Identity:     283/376 (75.3%)
# Similarity:   322/376 (85.6%)
# Gaps:           4/376 ( 1.1%)
# Score: 1431.5
#
#
#=======================================

SEQ ID NO: 1       1 MAICHHHQPSFTIPSSFPFTTNLSNKSQLHLPSSFRCNLSVTTNLEPE--     48
                     ||| .|:||.|...||...:|:|....:|||.||.|||:||.:.||||
SEQ ID NO: 3       1 MAI-RHYQPPFASTSSSISSTDLFKPPKLHLSSSVRCNISVASKLEPEPH     49

SEQ ID NO: 1      49 PVYTAVKSFAPATVANLGPGFDFLGCAVDGIGDYVTLKIDPQVHPGEVSI     98
                     ||:|:||||||||||||||||||||||:|||||||||.:||||.||.:||
SEQ ID NO: 3      50 PVFTSVKSFAPATVANLGPGFDFLGCAIDGIGDYVTLTVDPQVQPGRLSI     99

SEQ ID NO: 1      99 TEITGTGNSANKLSKNPIWNCAGIAAISVMKMLNIRSVGLSLSLEKGLPL    148
                     .||.|...|:.:||:||:|||||||||||||||.|||||||||:...|||
SEQ ID NO: 3     100 AEINGVDKSSKRLSRNPLWNCAGIAAISVMKMLKIRSVGLSLSINTCLPL    149

SEQ ID NO: 1     149 GSGLGSSAASAAAAAIAVNEIFGGKLPALDLVLAGLESEAKVSGYHADNI    198
                     ..|||||||||||||:||||||||||...||:|||||:|||:||||||||
SEQ ID NO: 3     150 RGGLGSSAASAAAAAVAVNEIFGGKLQDSDLILAGLEAEAKLSGYHADNI    199

SEQ ID NO: 1     199 APAIMGGFVLVRSYDPLELIPLQFPVDKNLYFVLVNPEFEAPTKKMRAAL    248
                     ||||||||||:|||||||||.|:||.:|||:||||||||:|.||||||.|
SEQ ID NO: 3     200 APAIMGGFVLIRSYDPLELISLKFPPEKNLFFVLVNPEFQAQTKKMRAVL    249

SEQ ID NO: 1     249 PKEITMSHHVWNSSQAGALVAAVLQGDLKGFGKALSSDKIVEPRRAPLIP    298
                     |.|||||.||||.|||.||||.||||||.|||||||||:|||||||||:|
SEQ ID NO: 3     250 PTEITMSDHVWNCSQAAALVAGVLQGDLVGFGKALSSDRIVEPRRAPLLP    299

SEQ ID NO: 1     299 GMDAVKKAALEAGAYGCTISGAGPTAVAVTDNEEKGREIGEKMVEAFMAE    348
                     ||:.|||||:|||||||||||:|||.|||||:|::||||||||||||:.:
SEQ ID NO: 3     300 GMEDVKKAAMEAGAYGCTISGSGPTVVAVTDDEDRGREIGEKMVEAFVEK    349

SEQ ID NO: 1     349 GNLKAVAMVKQLDRVGARLVSSISR-    373
                     |.|||:||||:|||||||::|.||.
SEQ ID NO: 3     350 GKLKALAMVKKLDRVGARVISRISSQ    375
```

Figure 2

```
Aligned_sequences: 2
# 1: SEQ ID NO: 1
# 2: SEQ ID NO: 3
# Matrix: EBLOSUM62
# Gap_penalty: 10.0
# Extend_penalty: 0.5
#
# Length: 376
# Identity:     283/376 (75.3%)
# Similarity:   322/376 (85.6%)
# Gaps:           4/376 ( 1.1%)
# Score: 1431.5
#
#
#=======================================

SEQ ID NO: 1       1 MAICHHHQPSFTIPSSFPFTTNLSNKSQLHLPSSFRCNLSVTTNLEPE--     48
                     ||| .|:||.|...||...:|:|....:|||.||.|||:||.:.||||  
SEQ ID NO: 3       1 MAI-RHYQPPFASTSSSISSTDLFKPPKLHLSSSVRCNISVASKLEPEPH     49

SEQ ID NO: 1      49 PVYTAVKSFAPATVANLGPGFDFLGCAVDGIGDYVTLKIDPQVHPGEVSI     98
                     ||:|:|||||||||||||||||||||||:|||||||||.:||||.||.:||
SEQ ID NO: 3      50 PVFTSVKSFAPATVANLGPGFDFLGCAIDGIGDYVTLTVDPQVQPGRLSI     99

SEQ ID NO: 1      99 TEITGTGNSANKLSKNPIWNCAGIAAISVMKMLNIRSVGLSLSLEKGLPL    148
                     .||.|...|:.:||:||:|||||||||||||||.|||||||||:...|||
SEQ ID NO: 3     100 AEINGVDKSSKRLSRNPLWNCAGIAAISVMKMLKIRSVGLSLSINTCLPL    149

SEQ ID NO: 1     149 GSGLGSSAASAAAAAIAVNEIFGGKLPALDLVLAGLESEAKVSGYHADNI    198
                     ..|||||||||||||:||||||||||...||:|||||:|||:||||||||
SEQ ID NO: 3     150 RGGLGSSAASAAAAAVAVNEIFGGKLQDSDLILAGLEAEAKLSGYHADNI    199

SEQ ID NO: 1     199 APAIMGGFVLVRSYDPLELIPLQFPVDKNLYFVLVNPEFEAPTKKMRAAL    248
                     ||||||||||:|||||||||.|:||.:|||:||||||||:|.||||||.|
SEQ ID NO: 3     200 APAIMGGFVLIRSYDPLELISLKFPPEKNLFFVLVNPEFQAQTKKMRAVL    249

SEQ ID NO: 1     249 PKEITMSHHVWNSSQAGALVAAVLQGDLKGFGKALSSDKIVEPRRAPLIP    298
                     |.|||||.||||.|||.||||.||||||.|||||||||:|||||||||:|
SEQ ID NO: 3     250 PTEITMSDHVWNCSQAAALVAGVLQGDLVGFGKALSSDRIVEPRRAPLLP    299

SEQ ID NO: 1     299 GMDAVKKAALEAGAYGCTISGAGPTAVAVTDNEEKGREIGEKMVEAFMAE    348
                     ||:.|||||:|||||||||||:|||.|||||:|::||||||||||||:.:
SEQ ID NO: 3     300 GMEDVKKAAMEAGAYGCTISGSGPTVVAVTDDEDRGREIGEKMVEAFVEK    349

SEQ ID NO: 1     349 GNLKAVAMVKQLDRVGARLVSSISR-     373
                     |.|||:||||:|||||||::|.||.
SEQ ID NO: 3     350 GKLKALAMVKKLDRVGARVISRISSQ     375
```

DOWNY MILDEW RESISTANT LETTUCE MUTANT

CROSS-REFERENCE TO RELATED APPLICATIONS

This application is a National Stage Entry of PCT/EP2019/075263, filed Sep. 19, 2019, which claims priority to EP application No. 18199989.7, filed Oct. 11, 2018, the disclosures of each of which are hereby incorporated by reference in their entireties.

FIELD OF THE INVENTION

The present invention relates to the field of modern lettuce breeding. Provided are lettuce plants, *Lactuca sativa* L., comprising one or more mutations in the endogenous homoserine kinase gene, whereby the mutations result in either a) one or more amino acid deletions, insertions or substitutions (replacements) in the homoserine kinase (HSK) protein compared to the wild type protein of SEQ ID NO: 1 (or a variant thereof) or b) reduced gene expression of the homoserine kinase gene. Preferably the mutation(s) in the HSK gene and the resulting one or more amino acid insertions, deletions or substitutions of the mutant protein compared to the wild type protein, or the resulting reduction in gene expression, result in an increase of the amino acid L-homoserine in the leaf tissue of lettuce plants, which comprise the mutant HSK allele in homozygous form, of a level of at least 5.0, preferably at least 6.0 or more preferably at least 7.0 nmol per milligram fresh weight. It was found that a minimal amount of in planta L-homoserine in the leaf tissue is needed in order for the plant to be resistant to the oomycete pathogen *Bremia lactucae.*

Lettuce has been previously described to contain an ortholog of the *Arabidopsis* homoserine kinase gene, namely the lettuce gene disclosed in EP1957655B1 (WO2007051626). When generating mutants in this gene, it was surprisingly found that none of the mutants accumulated L-homoserine in the leaf tissue.

It was further found that lettuce plants surprisingly comprise another gene encoding a 'homoserine kinase like protein', which is also expressed in leaf tissue. There seemed thus to be at least two genes expressed in leaf tissue, both of which encode putative homoserine kinase proteins. Upon analysis of the gene information present in the NCBI database, it became apparent that lettuce actually contains four loci in its genome with genes encoding putative homoserine kinase-like proteins, so even more genes could be involved.

The inventors surprisingly found that only mutations in one of these genes resulted in an accumulation of L-homoserine in the leaf tissue, when the mutant allele is in homozygous form. This was especially surprising as this meant that there was no redundancy of the genes, but that apparently the other HSK-like proteins have different functions. The invention, thus, relates to lettuce plants comprising two copies of a mutant allele of this gene, which when mutated resulted in accumulation of L-homoserine in the leaves, in their genome. The invention further relates to parts of these plants, to seeds, to propagation material, to the progeny of these plants, and use of the plants in breeding for resistance to *Bremia lactucae.*

Further, the inventors found that the HSK protein comprises 18 amino acids which directly interact with a substrate, either L-homoserine or ATP and that especially amino acid substitutions of one or more of these 18 amino acids (or amino acids close to these interacting amino acids) affect protein function and are thus preferred amino acids to substitute or to delete to increase L-homoserine in the leaf tissue to a sufficient amount to confer *Bremia* resistance.

BACKGROUND OF THE INVENTION

*Bremia lactucae*, an oomycete, is the causal organism of Downy Mildew infection in lettuce (*Lactuca sativa* L.). It constitutes a major problem for lettuce production in both glass house and open field conditions. *Bremia lactucae* is an obligate pathogen capable of infecting a lettuce plant in any growth stage from seedling to mature plant.

Downy mildew causes pale, angular, yellow areas bounded by veins on the upper leaf surfaces. Spore formation appears on the lower leaf surface soon after initial symptom development. The sporulating lesions eventually turn brown, and they may enlarge and coalesce. These symptoms typically occur first on the lower leaves of the lettuce, but under ideal conditions may move into the upper leaves of the head. When the oomycete progresses to this degree, the head cannot be harvested. Less severe damage can be handled by removal of the affected leaves. As such, every year this disease leads to millions of dollars of lost lettuce crop throughout the world.

Van Damme et al. 2005 (MPMI Vol. 18, No. 6, 2005, pp. 583-592) describe the identification of *Arabidopsis thaliana* mutants in a screen for reduced susceptibility to the downy mildew pathogen *Hyaloperonospora parasitica*. Ethyl methane sulfonate (EMS) mutants were generated in the highly susceptible *Arabidopsis* line Ler edsl-2. Eight downy mildew-resistant (dmr) mutants were analyzed in detail, corresponding to six different loci. Microscopic analysis showed that, in all mutants, *H. parasitica* growth was severely reduced. Resistance of dmr3, dmr4, and dmr5 was associated with constitutive expression of PR-1. Furthermore, dmr3 and dmr4, but not dmr5, also were resistant to *Pseudomonas syringae* and *Golovinomyces orontii*, respectively. However, enhanced activation of plant defense was not observed in dmr1, dmr2, and dmr6.

WO2007/051626 describes that the *Arabidopsis* mutants of Van Damme et al. 2005 (supra) contain mutations in the *Arabidopsis* HSK gene (homoserine kinase gene), which is also referred to as DMR-1 gene. The mutations of mutant plants dmr1 (mutation dmr1-1), dmr2 (mutation dmr1-2), dmr3 (mutation dmr1-3), dmr4 (mutations dmr1-4) and dmr5 (mutations dmr1-5) are all found to be single nucleotide changes in the *Arabidopsis* HSK gene, leading to single amino acid substitutions in the *Arabidopsis* HSK protein (see FIG. 1 of the patent application). HSK is described as being encoded by a single gene in *Arabidopsis* and in other plant species, except for potato, tobacco and poplar for which two HSK homologs have been identified. Apart from the mutations in the *Arabidopsis* HSK gene, the invention is said to relate to mutated versions of the HSK genes of *Lactuca sativa, Vitis vinifera, Cucumis sativus, Spinacia oleracea* and *Solanum lycopersicum* as shown in FIGS. 10-14 of WO2007/051626. A multiple sequence alignment of the *Arabidopsis* HSK protein and the HSK orthologs of other species, including lettuce, is shown in FIG. 1 of the patent application, wherein also the amino acid substitutions of the *Arabidopsis* dmr1 mutants are shown.

Van Damme et al. 2009 (The Plant Cell Vol. 21:2179-2189) further describe the *Arabidopsis* dmr1 mutants and show in supplement FIG. 2 an alignment with 11 other HSK proteins. The *Arabidopsis* mutations are all at amino acids that are identical or similar in these proteins. They show that five dmr1 mutants (dmr1-1, dmr1-2, dmr1-3, dmr1-4 and dmr1-5) have reduce HSK enzyme activity (FIG. 3) and that four mutants (dmr1-1, dmr1-2, dmr1-3, dmr1-4) accumulate L-homoserine in their tissue to a different extent without depleting downstream amino acids Threonine, Methionine and Isoleucine (FIG. 4). The conclusions they draw are that substitutions in the *Arabidopsis* HSK gene result in reduced enzyme activity and accumulation of homoserine in the tissue. All four mutants with increased homoserine in the chloroplast are concluded to be resistant to the oomycete *H. arabidopsis* as a result. In addition, the HSK protein is suggested to be an essential protein in *Arabidopsis*, because no null mutants were found.

Despite the extensive research in *Arabidopsis*, and identification of the HSK orthologs in lettuce in WO2007/051626, no lettuce plant with downy mildew resistance has been developed yet and there is still a need to provide lettuce plants having *Bremia lactucae* resistance.

Reyes-Chin-Wo et al. (Nature Communications 2017, 8:14953, Genome assembly with in vitro proximity ligation data and whole genome triplication in lettuce) identified three loci which contain genes characterized as 'homoserine kinase-like' hypothetical proteins. These loci are LOC111898998 (containing gene Lsat_1_v5_gn_2_1161.1 also referred to as Lsat_2X1161), LOC111899676 (containing gene Lsat_1_v5_gn_4_71321.1, also referred to as Lsat_4 X71321) and LOC111910590 (containing gene Lsat_1_v5_gn_8_121420.1, also referred to as Lsat_8 X121420). In addition there is another locus, LOC111917963, containing a homoserine kinase-like gene. The in vivo function of these hypothetical proteins is not known, as the name is based on similarity to conserved sequence domains or motifs.

Definitions

The indefinite article "a" or "an" does not exclude the possibility that more than one of the element is present, unless the context clearly requires that there be one and only one of the elements. The indefinite article "a" or "an" thus usually means "at least one".

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two or three loci or genes (or phenotypic characteristics due to these specific loci or genes), but which can otherwise differ from one another enormously as regards the other loci or genes in the genome.

"Lettuce" or "cultivated lettuce" or "cultivated *Lactuca sativa*" refers herein to plants of the species *Lactuca sativa* L. (or seeds from which the plants can be grown), and parts of such plants, bred by humans for food and having good agronomic characteristics. This includes any cultivated lettuce, such as breeding lines (e.g. backcross lines, inbred lines), cultivars and varieties of any type. Generally heading and non-heading types of lettuce are distinguished. Heading types include for example crisphead, butterhead and romaine (cos) types, while non-heading types include leaf-types. Cultivated lettuce plants are not "wild lettuce" plants or "wild *Lactuca*" plants, i.e. plants which generally have much poorer yields and poorer agronomic characteristics than cultivated plants and e.g. grow naturally in wild populations.

"Wild lettuce" or "wild *Lactuca*" accessions refers to plants of species other than cultivated *Lactuca sativa*, such as *Lactuca virosa, Lactuca serriola, Lactuca saligna, Lactuca perennis*, and others. Preferably, such wild lettuce comprises or consists of *Lactuca* species which are cross fertile with *L. sativa*, optionally with the aid of embryo rescue techniques (see Maisonneuve 1987, Agronomique 7: 313-319 and Maisonneuve et al. 1995, Euphytica 85:281-285) and/or chromosome doubling techniques (Thompson and Ryder 1961, US Dept Agric Tech Bul. 1224), or methods whereby genes can be transferred into *L. sativa* via a bridge species, such as *L. serriola* (Eenink et al. 1982, supra).

As used herein, the term "plant" includes the seed (from which the plant can be grown), the whole plant or any parts such as plant organs (e.g., harvested or non-harvested leaves, etc.), plant cells, plant protoplasts, plant cell- or tissue cultures, plant callus, plant cell clumps, plant transplants, seedlings, plant cells that are intact in plants, plant clones or micro-propagations, or parts of plants (e.g., harvested tissues or organs), such as plant cuttings, vegetative propagations, embryos, pollen, ovules, flowers, leaves, heads, seeds (produced on the plant after self-fertilization or cross-fertilization), clonally propagated plants, roots, stems, stalks, root tips, grafts, parts of any of these and the like, or derivatives thereof, preferably having the same genetic make-up (or very similar genetic make-up) as the plant from which it is obtained. Also any developmental stage is included, such as seedlings, cuttings prior or after rooting, mature and/or immature plants or mature and/or immature leaves. When "seeds of a plant" are referred to, these either refer to seeds from which the plant can be grown or to seeds produced on the plant, after self-fertilization or cross-fertilization.

"Somatic cells" and "reproductive cells" can be distinguished, whereby somatic cells are cells other than gametes (e.g. ovules and pollen), germ cells and gametocytes. Gametes, germ cells and gametocytes are "reproductive cells".

"Tissue Culture" or "cell culture" refers to an in vitro composition comprising isolated cells of the same or a different type or a collection of such cells organized into plant tissue. Tissue cultures and cell cultures of lettuce, and regeneration of lettuce plants therefrom, is well known and widely published (see, e.g., Teng et al., HortScience. 1992, 27(9): 1030-1032 Teng et al., HortScience. 1993, 28(6): 669-1671, Zhang et al., Journal of Genetics and Breeding. 1992, 46(3): 287-290).

"Harvested plant material" refers herein to plant parts (e.g., leaves, leaf parts or heads detached from the whole plant) which have been collected for further storage and/or further use.

"Harvested seeds" refers to seeds harvested from a line or variety, e.g., produced after self-fertilization or cross-fertilization and collected.

"Harvested leaves" or "harvested heads" as used herein refers to lettuce leaves, or leaf parts or heads, i.e., the plant without the root system, for example substantially all (harvested) leaves. Leaves may be whole or cut into parts.

"Progeny" or "progenies" or "descendants" as used herein refers to offspring, or the first and all further descendants derived from (obtained from) (derivable from or obtainable from) a plant of the invention that comprises (retains) the mutant HSK allele according to the invention. Progeny may be derived by regeneration of cell culture or tissue culture, or parts of a plant, or selfing of a plant, or by producing seeds of a plant. In further embodiments, progeny may also encompass lettuce plants derived from crossing of at least one lettuce plant with another lettuce plant of the same or another variety or (breeding) line, or wild *Lactuca* plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration or transformation. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Also double haploid plants are progeny.

A "plant line" or "breeding line" refers to a plant and its progeny being highly uniform in plant phenotype. As used herein, the term "inbred line" refers to a plant line which has been repeatedly selfed and is nearly homozygous for all alleles. Thus, an "inbred line" or "parent line" refers to a plant which has undergone several generations (e.g. at least 4, 5, 6, 7 or more) of inbreeding, resulting in a plant line with a high uniformity.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"Hybrid" refers to the seeds harvested from crossing one plant line or variety with another plant line or variety, and the plants or plant parts grown from said seeds.

"F1 hybrid" plant (or F1 hybrid seed) is the generation obtained from crossing two non-isogenic inbred parent lines. Thus, F1 hybrid seeds are seeds from which F1 hybrid plants grow.

An "interspecific hybrid" refers to a hybrid produced from crossing a plant of one species, e.g. *L. sativa*, with a plant of another species, e.g. *L. virosa*.

"Crossing" refers to the mating of two parent plants. Equally "Cross-pollination" refers to fertilization by the union of two gametes from different plants.

"Selfing" refers to the self-pollination of a plant, i.e. to the union of gametes from the same plant.

"Backcrossing" refers to a breeding method by which a trait, such as a mutant HSK allele according to the invention, can be transferred from one genetic background (also referred to as "donor") into another genetic background (also referred to as "recurrent parent"), e.g. into a *Bremia* susceptible lettuce line or variety. An offspring of a cross between the donor and the recurrent parent (e.g. an F1 plant; or an F2 plant or F3 plant, etc., obtained from selfing the F1) is "backcrossed" to the recurrent parent, e.g. to the *Bremia*-susceptible parent. After repeated backcrossing, the trait of the donor will have been incorporated into the recurrent parent background. The terms "gene converted" or "conversion plant" in this context refer to plants which are developed by backcrossing wherein essentially all of the desired morphological and/or physiological characteristics of the recurrent parent are recovered in addition to the trait (e.g. the mutant HSK allele) transferred from the donor parent.

The term "traditional breeding techniques" encompasses herein crossing, backcrossing, selfing, selection, chromosome doubling, double haploid production, embryo rescue, the use of bridge species, protoplast fusion, marker assisted selection, mutation breeding etc. as known to the breeder (i.e. methods other than genetic modification/transformation/transgenic methods).

"Regeneration" refers to the development of a plant from in vitro cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting off) leaf, pollen, embryo, cotyledon, hypocotyl, cells, protoplasts, meristematic cell, root, root tip, pistil, anther, flower, shoot tip, shoot, stem, fruit, and petiole. When a whole plant is regenerated by vegetative propagation, it is also referred to as a "vegetative propagation" or a "vegetatively propagated plant".

"Single (or double or triple) locus converted (conversion) plant" refers to plants which are developed by plant breeding techniques comprising or consisting of backcrossing, wherein essentially all of the desired morphological and/or physiological characteristics of a lettuce plant are recovered in addition to the characteristics of the single locus (or two or three loci) having been transferred into the plant via e.g. the backcrossing technique.

"Transgene" or "chimeric gene" refers to a genetic locus comprising a DNA sequence which has been introduced into the genome of a lettuce plant by transformation. A plant comprising a transgene stably integrated into its genome is referred to as "transgenic plant".

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternative forms of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimizes the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids an Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Wild type allele" of a HSK gene refers to the functional allele, encoding a wild type HSK protein of SEQ ID NO: 1 (or a protein comprising at least 80%, 85%, 90%, 95%, 98% or 99% sequence identity to SEQ ID NO: 1), which when its enzymatic activity is reduced (e.g. due to one or more amino acids being inserted, deleted or replaced compared to the wild type protein) or when its gene expression is knocked-down in a lettuce plant leads to (in a plant homozygous for the mutant allele) an accumulation of L-homoserine in the leaf tissue.

"Mutant allele" of a HSK gene refers to an allele encoding a protein comprising one or more amino acids inserted, deleted or replaced compared to the wild type HSK protein of SEQ ID NO: 1 (or a protein comprising at least 80%, 85%, 90%, 95%, 98% or 99% sequence identity to SEQ ID NO: 1), or comprising reduced gene expression (knock down) compared to the wild type allele e.g. due to mutations in regulatory elements, such as the promoter sequence, enhancer sequences and the like.

"Knock-down" refers to reduced gene expression compared to the wild type allele, while "knock-out" refers to no gene expression (e.g. mRNA transcript) being detectable anymore.

"Reduced activity" or "reduced enzymatic activity" of a HSK protein refers to the protein having reduced enzymatic activity, whereby L-homoserine accumulates in the leaf tissue, when the mutant allele is in homozygous form. "Reduced enzymatic activity" does not encompass "no enzymatic activity".

FIGURES

FIG. 1 shows a pairwise amino acid sequence alignment of the lettuce HSK protein of SEQ ID NO: 1 with the protein of SEQ ID NO: 3, which when mutated does not lead to an accumulation of L-homoserine. In the HSK protein of SEQ ID NO: 1 three amino acids are highlighted in bold, which lead to an increase in L-homoserine when substituted (and when the mutant allele is in homozygous form). Mutant E238K resulted in an amount of 0.38 nmol/mgFW homoserine, mutant M244I resulted in an amount of 4.41 nmol/mgFW and mutant R245K resulted in an amount of 19.46 nmol/mgFW. ("nmol/mgFW" refers to nano mole per milligram of Fresh Weight of tissue; to convert the amount of L-homoserine from nmol/mgFW into ng/mgFW, multiplication by 119 is needed).

FIG. 2 shows the same pairwise alignment as FIG. 1, but herein the amino acids in SEQ ID NO: 1 are highlighted in bold, which interact with L-homoserine or ATP (Adenosine tri-phosphate). Substitution or deletion of any one of these interacting amino acids by another amino acid, or optionally substitution or deletion of an amino acid located 1, 2, 3 or 4 positions either before or after the interacting amino acid, will reduce the in vivo activity of the HSK enzyme, i.e. L-homoserine will accumulate.

DETAILED DESCRIPTION

The instant inventors surprisingly found that in cultivated lettuce (*Lactuca sativa*) a gene on chromosome 8 is expressed in leaf tissue and encodes a functional HSK protein, which is the ortholog of the *Arabidopsis* HSK gene.

Based on the previous disclosure of the lettuce HSK ortholog in WO2007/051626 (FIG. 10), it was expected that mutations in the gene on chromosome 4 would affect chloroplastic homoserine accumulation and that this in turn could affect *Bremia lactucae* resistance in lettuce. However, this was surprisingly not the case.

Upon further analysis, the lettuce genome was described to contain four loci with putative HSK-like genes.

As at least two (but maybe more) HSK-like proteins appear to be present in the chloroplasts of lettuce, only mutating several genes could be expected to reduce the enzyme activity in the chloroplast sufficiently to result in an overall increase of homoserine. A similar situation had been described for the DMR6 gene in crops where two DMR6 genes were found, see e.g. WO2015193418, where resistance against the oomycete *Phytophthora infestans* requires downregulation of two DMR6-like genes.

It was surprisingly found that, however, no such functional redundancy exists in lettuce and that mutations of only the gene on chromosome 8 are sufficient to increase L-homoserine in leaf tissue.

TABLE 1

Percentage protein sequence identity, determined using pairwise protein alignments using EMBOSS-Needle (default parameters)

| | Arabidopsis AT2G17265 | Lettuce HSK-like protein_Chr4 (XP_023751301.1) | Lettuce HSK-like protein_Chr8 (XP_023762184.1) | Lettuce protein of FIG. 10 of WO2007/051626 |
|---|---|---|---|---|
| Arabidopsis HSK protein AT2G17265 | 100% | 66.4% | 72.6% | 66.4% |
| Lettuce HSK-like protein_Chr4 (XP_023751301.1) SEQ ID NO: 3 herein | | 100% | 75.3% | 99.2% |
| Lettuce HSK-like protein_Chr8 (XP_023762184.1) SEQ ID NO: 1 herein | | | 100% | 74.7% |
| FIG. 10 of WO2007/051626 | | | | 100% |

None of the mutants comprising single amino acid substitutions in the protein encoded by the gene on chromosome 4 had an in planta increase of L-homoserine (despite the fact that the single amino acid substitutions were predicted to reduce the protein activity), while three mutants comprising single amino acid substitutions in the protein on chromosome 8 had an increased in planta L-homoserine level. See Examples. These results surprisingly showed that single amino acid substitutions in the HSK-like gene on chromosome 8 are sufficient to lead to an in planta increase in L-homoserine, while the gene on chromosome 4 may remain unmutated (wild type).

A further surprising finding was that a minimum level of in planta homoserine accumulation is needed to result in the lettuce plant being resistant against *Bremia lactucae*. The mutant which resulted in an amount of L-homoserine of 0.38 nmol/mg FW tissue (E238K) and the mutant which resulted in an amount of 4.41 nmol/mgFW tissue (M244I) did not lead to *Bremia lactucae* resistance. See Examples.

Therefore, in one aspect a plant of the species *Lactuca sativa* is provided, which is homozygous for a mutant allele of the homoserine kinase gene, which mutant allele encodes a mutant homoserine kinase protein comprising one or more amino acid inserted, deleted or replaced (substitutions) compared to the wild type homoserine kinase protein of SEQ ID NO: 1, or compared to a wild type homoserine kinase protein comprising at least 85%, 90%, 95%, 96%, 97%, 98% or 99% sequence identity to SEQ ID NO:1, or which mutant allele comprises a reduced gene expression compared to the wild type allele, said mutant allele resulting in the leaf tissue of said lettuce plant comprising an amount of L-homoserine of at least 5.0 nmol per mg fresh weight (more preferably at least 10.0, 15.0, 16.0, 17.0, 18.0 or 19.0 or more nmol per mg fresh weight), while a plant heterozygous for the mutant allele or lacking the mutant allele (i.e. homozygous for the wild type allele encoding the wild type HSK protein of e.g. SEQ ID NO: 1) does not accumulate L-homoserine in the leaf tissue.

A wild type homoserine kinase protein of SEQ ID NO: 1, or a wild type homoserine kinase protein comprising at least 85%, 90%, 95%, 96%, 97%, 98% or 99% sequence identity to SEQ ID NO:1 (also referred to as wild type HSK protein variant or simply "variant of SEQ ID NO: 1"), refers to a fully functional protein, i.e. which does not have reduced enzymatic activity and converts L-homoserine into phospho-homoserine (phosphorylation). When present in the plant e.g. in homozygous form, e.g. in a normal lettuce breeding line or variety, no L-homoserine accumulates in the leaf tissue. The functionality of a homoserine kinase protein or protein variant can thus be seen in plant in vivo, either being present endogenously or overexpressed in a transgenic lettuce plant, or alternatively by in vitro assays, by e.g. measuring the consumption of ATP of the recombinantly produced protein, which is an indirect measure of enzymatic activity as ATP is used for phosphorylation of homoserine. Such in vitro assays are known in the art, e.g. described in Van Damme et al. 2009 for the *Arabidopsis* HSK enzyme (supra, page 2187 under "HSK Recombinant Protein Production and Enzyme assay").

The homoserine kinase gene or allele encoding a wild type HSK protein is, accordingly, referred to as a wild type homoserine kinase gene or allele. As the coding sequence of the gene contains no intron sequences, the genomic DNA and the coding DNA (cDNA) are identical. The mRNA encoding the protein is thus also identical to the genomic DNA and cDNA except that off course the nucleoside T (thymine) is replaced by U (uracil) in the mRNA. In SEQ ID NO: 2 the genomic DNA and cDNA encoding the protein of SEQ ID NO: 1 is shown.

A plant comprising a fully functional, wild type homoserine kinase gene in homozygous form is also referred to a "wild type lettuce plant". This is in contrast to a plant which comprises a mutant allele of the homoserine kinase gene, which mutant allele encodes a mutant homoserine kinase protein comprising one or more amino acid insertions, deletions or substitutions compared to the wild type homoserine kinase protein and wherein the mutant homoserine kinase protein has reduced enzymatic activity in vivo, resulting in an accumulation of L-homoserine in the leaf tissue, when the mutant allele is in homozygous form, as the conversion of homoserine to phospho-homoserine occurs to a lower extent than in wild type plants. When the mutant allele is in heterozygous form (i.e. the plant comprises only one copy of the mutant allele and one copy of the wild type allele, homoserine will not accumulate, as the fully functional wild type protein still carries out the conversion.

Alternatively a plant which comprises a mutant allele of the homoserine kinase gene is a plant in which the gene expression is reduced (knocked-down) compared to the wild type allele, e.g. the mutant allele comprises one or more mutations in the regulatory elements, such as the promoter sequence.

In other words, the lettuce plant according to the invention comprises a mutant homoserine kinase allele, which mutant allele either a) encodes a mutant homoserine kinase protein comprising one or more amino acid insertions, deletions or substitutions compared to the wild type homoserine kinase protein of SEQ ID NO: 1, or compared to a variant wild type homoserine kinase protein comprising at least 85%, 90%, 95%, 96%, 97%, 98% or 99% sequence identity to SEQ ID NO:1, said mutant protein comprises reduced enzymatic activity compared to the wild type protein, or b) which mutant allele comprises reduced gene expression and therefore a lower amount of wild type protein, and as a result of a) or b) leads to accumulation of L-homoserine in the leaf tissue when the mutant allele is in homozygous form (while a plant homozygous for the wild type allele does not lead to homoserine accumulation in the leaves).

The reduced enzymatic activity of a mutant homoserine kinase protein or the reduced gene expression can thus be seen in a plant in vivo, when present in homozygous form in a lettuce plant (e.g. the degree of reduction of enzymatic activity or reduced gene expression will be reflected in the amount of homoserine accumulating), or alternatively by in vitro assays, by e.g. measuring the consumption of ATP of the recombinantly produced mutant HSK protein, which is an indirect measure of enzymatic activity, as ATP is used for phosphorylation of homoserine. Such in vitro assays are known in the art, e.g. described in Van Damme et al. 2009 for the *Arabidopsis* HSK enzyme (supra, page 2187 under "HSK Recombinant Protein Production and Enzyme assay"). Thus, the enzymatic activity of a recombinantly produced wild type homoserine kinase protein can be compared to the enzymatic activity of one or more mutant proteins and also the activity of different mutant HSK proteins can be compared. Some amino acid substitutions have a more profound effect on reducing the enzymatic activity than others, as can be seen in the Examples.

As mentioned, the degree to which the enzymatic activity of the mutant homoserine kinase protein is reduced will vary, depending on the effect of the amino acid insertion, deletion or substitution on the protein. As an indication regarding whether an amino acid substitution will likely affect protein activity, various computer programs can be used, such as SIFT analysis (Sorting Intolerant from Tolerant, see www at //sift.bii.a-star.edu.sg/) or PROVEAN (www at provean.jcvi.org/index.php) can be used. However, whether the mutation has the desired effect and especially whether the enzymatic activity is sufficiently reduced to lead to a minimum desired accumulation of homoserine, e.g. at least 5.0 nmol/mg FW, always needs to be confirmed experimentally.

Interestingly, the three lettuce mutants found to lead to an increase in L-homoserine, were not in the two conserved kinase domains, but in-between the two conserved kinase domains, i.e. in-between the N terminal kinase domain and the C terminal kinase domain. The protein of SEQ ID NO: 1 contains a "GHMP kinase N terminal domain" starting at amino acid 140 and ending at amino acid 205 (Pfam domain PF00288) and a "GHMP kinase C terminal domain" starting at amino acid 268 and ending at amino acid 345 (Pfam domain PF08544).

Also, the three mutants identified resulted in very different levels of homoserine accumulation. Mutant E238K resulted in only 0.38 nmol/mgFW of L-homoserine, while the other two mutants resulted in an accumulation of L-homoserine to 4.41 (mutant M244i) and 19.46 nmol/mgFW (mutant R245K).

The three dimensional structure of the enzyme was analyzed (see Examples), and surprisingly it was found that 18 amino acids distributed across the entire protein were actually interacting with L-homoserine or with ATP. Amongst these 18 amino acids was the amino acid R245 of SEQ ID NO: 1. The three dimensional structure therefore explained why the substitution of R245 had a profound effect on enzymatic activity and resulted in a much higher L-homoserine accumulation than the other mutants, which were substitutions in amino acids which did not interact with L-homoserine or ATP.

Therefore, in one aspect a plant of the species *Lactuca sativa* is provided, which is homozygous for a mutant allele of the homoserine kinase gene, which mutant allele encodes a mutant homoserine kinase protein comprising one or more amino acid insertions, deletions or substitutions compared to the wild type homoserine kinase protein of SEQ ID NO: 1, or compared to a wild type homoserine kinase protein comprising at least 85%, 90%, 95%, 96%, 97%, 98% or 99% sequence identity to SEQ ID NO:1, said mutant allele resulting in the leaf tissue of said lettuce plant comprising an amount of L-homoserine of at least 5.0 nmol per mg fresh weight, while a plant heterozygous for the mutant allele or lacking the mutant allele (i.e. homozygous for the wild type allele encoding the wild type HSK protein of e.g. SEQ ID NO: 1) does not accumulate L-homoserine in the leaf tissue, wherein said one or more amino acid substitutions, or deletions, are selected from the amino acids N64 (Asn at position 64 of SEQ ID NO: 1), D70 (Asp at position 70 of SEQ ID NO: 1), N118 (Asn at position 118 of SEQ ID NO: 1), C119 (Cys at position 119 of SEQ ID NO: 1), K144 (Lys at position 144 of SEQ ID NO: 1), G149 (Gly at position 149 of SEQ ID NO: 1), G151 (Gly at position 151 of SEQ ID NO: 1), L152 (Leu at position 152 of SEQ ID NO: 1), G153 (Gly at position 153 of SEQ ID NO: 1), S154 (Ser at position 154 of SEQ ID NO: 1), S155 (Ser at position 155 of SEQ ID NO: 1), S158 (Ser at position 158 of SEQ ID NO: 1), D196 (Asp at position 196 of SEQ ID NO: 1), N197 (Asn at position 197 of SEQ ID NO: 1), T241 (Thr at position 241 of SEQ ID NO: 1), R245 (Arg at position 245 of SEQ ID NO: 1), R293 (Arg at position 293 of SEQ ID NO: 1) and A320 (Ala at position 320 of SEQ ID NO: 1) being replaced by a different amino acid, or being deleted.

Other amino acid substitutions or deletions may also lead to an increase in homoserine. One way to finally find out whether a mutant will result in an increase in homoserine, and to what extent, is to generate the mutant and then to test the homoserine level. The skilled person can do this without undue burden by generating mutants and identifying lettuce plants comprising mutations which result in e.g. substitutions of particular amino acids in the protein of SEQ ID NO: 1 (or in a variant thereof), such as for example in any of the amino acids which interact with homoserine or ATP as indicated above, or amino acids near any of the 18 'interacting' amino acids, such as the amino acids located 1, 2, 3 or 4 positions before or after the 'interacting' amino acid.

In one aspect a lettuce plant is provided comprising a mutant allele of a homoserine kinase gene, which mutant allele encodes a mutant homoserine kinase protein comprising one or more amino acid substitutions compared to the wild type homoserine kinase protein of SEQ ID NO: 1, or compared to a variant wild type homoserine kinase protein comprising at least 85%, 90%, 95%, 96%, 97%, 98% or 99% sequence identity to SEQ ID NO:1, wherein the mutant homoserine kinase protein comprises one or more amino acids, selected from the group consisting of N64 (Asn at position 64 of SEQ ID NO: 1), D70 (Asp at position 70 of SEQ ID NO: 1), N118 (Asn at position 118 of SEQ ID NO: 1), C119 (Cys at position 119 of SEQ ID NO: 1), K144 (Lys at position 144 of SEQ ID NO: 1), G149 (Gly at position 149 of SEQ ID NO: 1), G151 (Gly at position 151 of SEQ ID NO: 1), L152 (Leu at position 152 of SEQ ID NO: 1), G153 (Gly at position 153 of SEQ ID NO: 1), S154 (Ser at position 154 of SEQ ID NO: 1), S155 (Ser at position 155 of SEQ ID NO: 1), S158 (Ser at position 158 of SEQ ID NO: 1), D196 (Asp at position 196 of SEQ ID NO: 1), N197 (Asn at position 197 of SEQ ID NO: 1), T241 (Thr at position 241 of SEQ ID NO: 1), R245 (Arg at position 245 of SEQ ID NO: 1), R293 (Arg at position 293 of SEQ ID NO: 1) and A320 (Ala at position 320 of SEQ ID NO: 1), being substituted by a different amino acid. Optionally, alternatively or in addition an amino acid 1, 2, 3 or 4 positions preceding or following the above amino acids may be substituted. Alternatively, one or more of the above amino acids are deleted in the mutant protein, whereby the interaction with L-homoserine or ATP will be impaired and the enzymatic activity will be reduced.

As described above, a mutant allele may either result in a HSK protein having reduced enzymatic activity or may result in a reduced gene expression of the wild type allele and thereby a reduced amount of wild type HSK protein in the tissue. It is preferred however, that the mutant HSK protein still has some enzymatic activity or that the mutant allele still has some level of gene expression, as it is believed that the lettuce plant comprising the mutant allele in homozygous form will otherwise show severe negative side effect on e.g. growth and vitality of the plant. So, neither a loss-of-function protein nor a knock-out of gene expression are preferred herein. In one aspect the mutant HSK protein has an enzymatic activity which is at least 40%, 50%, 60%, 70% or 80%, or 90% of the enzymatic activity of the wild type HSK protein, but which is less than 100% of the enzymatic activity of the wild type protein. In one aspect the mutant allele expresses at least 40%, 50%, 60%, 70%, 80% or 90% of the mRNA transcript expressed by the wild type allele, but expresses less than 100% of the mRNA transcript of the wild type allele.

Preferably the lettuce plant comprises the mutant allele in homozygous form, resulting in an accumulation of L-homoserine. Preferably at least 5.0 nmol/mg/FW L-homoserine, at least 6.0 nmol, 7.0 nmol, 8.0 nmol, 9.0 nmol, 10.0 nmol, 11.0 nmol, 12.0 nmol, 13.0 nmol, 14.0 nmol, 15.0 nmol, 16.0 nmol, 17.0 nmol, 18.0 nmol or at least 19.0 nmol accumulate in planta.

It is thus understood that the amino acid insertion, deletion or substitution does in one aspect not result in a completely inactive homoserine kinase protein and that the mutant allele is not a knock-out allele, as this is thought to have severe negative effects on the fitness of the plant and may even be lethal to the plant.

In a preferred aspect, the mutant homoserine kinase protein is reduced in enzymatic activity, or the gene expression is reduced to such an extent that the amount of L-homoserine accumulating in leaf tissue of plants homozygous for the mutant allele is at least 5.0 nmol per mg fresh weight of leaf tissue, more preferably at least 6.0, 7.0 or 8.0 nmol per mg fresh weight of leaf tissue, more preferably at least 9.0 nmol or 10.0 nmol or 15.0 nmol, 16.0 nmol, 17 nmol, 18 nmol, or even at least 19.0 nmol per mg fresh weight of leaf tissue.

In one aspect the mutant allele (when in homozygous form) does not result in an accumulation of L-homoserine of more than 50 or 40 nmol per mg FW, preferably not more than 30 nmol per mg FW, not more than 25.0 nmol per mg FW, or not more than 24.0 nmol, 23.0 nmol, 22.0 nmol, 21.0 nmol or 20.0 nmol per mg/FW. In particular, the homoserine level should not have a negative effect on other characteristics of the plant, such as the growth and development of the plant, yield, etc., while still providing resistance against *Bremia.*

In one aspect the amount of at least 5.0 nmol/mg/FW, or more (as indicated above), of L-homoserine accumulating in the leaf tissue of a plant is an average of measurements of at least two, three, four or five independent leaf samples of the plant comprising the mutant allele in homozygous form.

The skilled person can generate such mutants as described herein, e.g. by screening a mutant lettuce population (e.g. a TILLING population) for mutants in the homoserine kinase gene encoding the protein of SEQ ID NO: 1 (or a variant thereof), optionally selfing the mutants to generate homozygous plants if the plants were not yet homozygous, and analyzing the amount of homoserine in the leaf tissue of said plants. The plants comprising mutations which result in at least 5.0 nmol per milligram fresh weight of the lettuce leaf tissue (or at least another minimal amount as referred to above) can then be selected. Optionally the skilled person can then test whether these plants comprise resistance against one or more races of *Bremia lactucae*, using e.g. a Leaf Disc Test as described in the Examples. It is understood that, if the plant line or variety in which the mutant was generated, already contains resistance against one or more *Bremia* races, then the effect a mutation against the resistance cannot be tested in that genetic background and the mutation needs first to be crossed into a line which is susceptible against the *Bremia* race(s).

The Leaf Disc Test (LDT) described in the Examples has the advantage over other tests, such as seedling tests (also known as cotyledons test) that it provides a good correlation with field resistance against *Bremia lactucae.*

In one aspect the lettuce plant which is homozygous for a mutant HSK allele, as described above, comprises an amount of L-homoserine in leaf tissue of at least 5.0 nmol per mg fresh weight of leaf tissue, more preferably at least 6.0, 7.0 or 8.0 nmol per mg fresh weight of leaf tissue, more preferably at least 9.0 nmol or 10.0 nmol, 11.0 nmol, 12.0 nmol, 13.0 nmol, 14.0 nmol or 15.0 nmol or 16.0 nmol or 17.0 nmol or 18.0 nmol even at least 19 nmol per mg fresh weight of leaf tissue and is preferably resistant to *Bremia lactucae*, preferably at least to one or more races of *Bremia lactucae*, e.g. at least race BI:25. In one aspect the leaves of the plant do not show any sporulation of the *Bremia lactucae* race with which they were inoculated or infected, while the susceptible control plants and/or plants heterozygous for the mutant allele show sporulation when e.g. using a *Bremia lactucae* test Leaf Disc Test as described in the Examples. It is understood that the *Bremia* resistance is caused by the amount of L-homoserine accumulated in the leaf tissue, and not by any background resistance gene present in the plant.

As mentioned, the homoserine kinase gene on chromosome 4, encoding the protein of SEQ ID NO: 3, is not effective in altering homoserine kinase levels in the plant when mutated. Thus, in one aspect the plant according to the invention, comprising a mutant allele in the homoserine kinase gene on chromosome 8 in homozygous form, as described above, further comprises a wild type (non-mutated) homoserine kinase gene on chromosome 4, e.g. comprises the wild type allele of the homoserine kinase gene encoding the wild type homoserine kinase protein of SEQ ID NO: 3, or encoding another functional variant thereof, such as a protein comprising at least 85%, 90%, 95% or more sequence identity to SEQ ID NO: 3. The genomic coding sequence, which corresponds to the cDNA sequence, encoding the protein of SEQ ID NO: 3 is shown in SEQ ID NO: 4. Thus, in one aspect the lettuce plant according to the invention comprises the sequence of SEQ ID NO: 4 in its genome, preferably in homozygous form.

In a specific aspect of the invention the plant of the species *Lactuca sativa* which is homozygous for a mutant allele of the homoserine kinase gene, which mutant allele encodes a mutant homoserine kinase protein comprising one or more amino acid substitutions or deletions compared to the wild type protein of SEQ ID NO: 1 (or a variant thereof), comprises a change of Arginine (Arg, R) at amino acid number 245 of SEQ ID NO: 1 to a different amino acid, preferably to Lysine (Lys, K), or any other amino acid, or comprises a deletion of the Arginine at amino acid number 245 of SEQ ID NO: 1. Thus, the mutant allele results in a mutant protein, which comprises a single amino acid substitution of amino acid number 245 in SEQ ID No: 1 or comprises a deletion of one or more amino acids, whereby amino acid 245 of SEQ ID NO: 1 is deleted. In one aspect the amino acid substitution is a R245K substitution. This particular mutant lettuce plant (comprising the mutant allele in homozygous form) was found to contain L-homoserine in an amount of 19.46 nmol per mg/fresh weight of leaf tissue. The mutant also did not show any sporulation of *Bremia lactucae* BI:25, in the Leaf Disc Test described in the Examples, while the susceptible controls (containing only wild type HSK alleles) showed 100% sporulation.

Two different mutants, mutant E238K and (comprising a E238K substitution, i.e. Glutamic acid, Glu, at amino acid 238 being substituted by Lysine, Lys) in SEQ ID NO: 1 and mutant M244i (comprising a M244i substitution, i.e. Methionine, Met, at amino acid 244 being substituted by Isoleucine, I) in SEQ ID NO: 1 showed an increase in L-homoserine of 0.38 nmol/mg FW and 4.41 nmol/mg/FW respectively. Surprisingly, these two mutants were both susceptible to *Bremia lactucae*. Mutant E238K showed 100% sporulation in the Leaf Disc Test with race BI:25EU in the Examples, the same as the susceptible controls. Likewise mutant M244i was susceptible to *Bremia* race BI:26EU showing significant sporulation.

As mentioned, the plants according to the invention, accumulating at least 5.0 nmol/mg FW of L-homoserine (or at least 10 nmol/mg FW, etc. as described), are preferably resistant against one or more races of *Bremia lactucae*. *Bremia lactucae* comprises different races, referred to as BI:X, where X is a number from 1 to 35 for European races and a number from 1 to 9 for US races. The European races are designated with the suffix 'EU', while the US races are designated with the suffix 'US'. In Europe the races BI:16-35EU are important (this designation excludes BI:19EU and BI:28EU, which are no longer existent), while BI:1-15EU are no longer important in the field. In the USA BI:1-4US have less importance, as they are no longer detected in the western USA, while BI:5-9US are important races.

Thus, in one aspect the plants according to the invention, which comprise at least 5 nmol per mg FW homoserine in their leaf tissue, comprise resistance against one or more or all races selected from BI16—35EU and BI:5-9US. Although the mutant R245K has so far only been shown to be resistant against *Bremia* race BI:25EU, it is expected that the mutant will likewise be resistant against the other races of *Bremia lactucae*, as L-homoserine is expected to negatively affect the reproduction of this pathogen.

Resistance against a race of *Bremia lactucae* is herein in one aspect defined as no *Bremia* spores being produced on the leaves or leaf parts under conditions wherein the susceptible control, e.g. the same plant lacking the mutant HSK allele, produces spores and is fully susceptible to the race. For example, in the Leaf Disc Test described in the Examples, the leaf discs of the resistant plant would show no spores (0% sporulation), while the leaf discs of the susceptible control show 100% sporulation.

Preferably the resistant lettuce plants according to the invention also show no sporulation when exposed to *Bremia lactucae* races in the field or in other environments, such as the glasshouses or tunnels.

Thus, in one aspect the lettuce plant comprising the mutant HSK allele in homozygous form comprises an amount of said L-homoserine in the leaf tissue which is high enough to prevent sporulation of *Bremia lactucae* under conditions where the susceptible control plant shows the expected sporulation. The skilled person can generate different mutants, which result in the accumulation of different amounts of L-homoserine when the allele is in homozygous form and then test whether the amount of L-homoserine is high enough to prevent sporulation of *Bremia lactucae*, e.g. in a Leaf Disc Test as described in the examples or another test. Importantly the susceptible control, which comprises wild type, non-mutated HSK alleles, such as variety Wendel or Cervino or others, are completely susceptible in the test and show e.g. 100% sporulation in the Leaf Disc Test (see Examples).

In one aspect a plant of the species *Lactuca sativa* is provided, which is homozygous for a mutant allele of the homoserine kinase gene, which mutant allele encodes a mutant homoserine kinase protein comprising one or more amino acid insertions, deletions or substitutions compared to the wild type protein of SEQ ID NO: 1, or comprising reduced gene expression of the mutant allele, said mutant allele resulting in the leaf tissue of said lettuce plant comprising an amount of L-homoserine which is high enough to result in the absence of *Bremia lactucae* sporulation when the plant or plant parts are tested under conditions wherein the susceptible control shows the expected phenotype (e.g. 100% sporulation in the Leaf Disc Test).

In one aspect the lettuce plant according to the invention, which comprises a mutant allele which encodes a mutant homoserine kinase protein comprising one or more amino acid substitutions compared to the wild type protein of SEQ ID NO: 1, does not comprise an amino acid substitution at amino acid 316 of SEQ ID NO: 1. Thus, in one aspect, amino acid 316 of SEQ ID NO: 1 is a Threonine (Thr, T).

Preferably the mutation in the allele of the homoserine kinase gene described herein is induced by human intervention, such as mutagenesis (exposure to a mutagenic agent, e.g. radiation, chemical mutagens, etc.) or targeted gene modification techniques, such as CRISPR/Cas or TALENS or others. In one aspect the mutant allele is, thus, not a naturally occurring mutant allele, i.e. it is not derived from natural populations or breeding populations. The mutation in the HSK allele is, therefore, in one aspect not a naturally occurring mutation, but a mutation induced by human intervention.

In one aspect the plant comprising the mutant allele is, therefore, not exclusively obtained by an essentially biological process, such as crossing and selection, but generation of the mutant allele involved a technical step. It is understood that the mutant allele may be transferred into any other lettuce plant through crossing and selection.

Further encompassed herein are seeds from which a plant according to the invention grows, as well as any parts of a plant according to the invention, such as lettuce heads, leaves, baby leaf leaves, flowers, pollen, roots, ovaries, cells, embryos, etc.

The plant or plant parts comprise at least one copy of the mutant HSK allele in their genome, preferably two copies.

Also lettuce plants and plant parts comprising a mutant HSK allele as described herein in heterozygous form are part of the invention, as these are useful in breeding plants which comprise the mutant allele in homozygous form.

In one aspect also non-propagating cells of a lettuce plant according to the invention are provided, which comprise at least one copy, preferably two copies of the mutant HSK allele in their genome. Non-propagating cells are cells which cannot regenerate into a lettuce plant.

Also tissue- or cell cultures comprising tissues or cells of a lettuce plant according to the invention are provided herein.

Feed or food products comprising cells or tissues of a lettuce plant according to the invention are also provided herein.

The cultivated lettuce plant according to the invention may be of any type, such as butterhead, iceberg, etc. The mutant allele can easily be transferred from one lettuce plant into another by e.g. backcrossing. In this way many different lettuce types and varieties can be generated, which comprise *Bremia* resistance due to the presence of a mutant allele according to the invention in homozygous form.

Methods According to the Invention

In one aspect a method for generating and/or selecting a lettuce plant comprising at least 5.0 nmol L-homoserine per mg fresh weight of leaf tissue, more preferably at least 6.0, 7.0 or 8.0 nmol L-homoserine per mg fresh weight of leaf tissue, more preferably at least 9.0 nmol or 10.0 nmol or 15.0 nmol or even at least 19.0 nmol L-homoserine per mg fresh weight of leaf tissue, is provided comprising the steps:

a) Providing a plurality of lettuce plants which are homozygous for a mutant allele of the homoserine kinase gene, which mutant allele encodes a mutant homoserine kinase protein comprising one or more amino acid insertions, deletions or substitutions compared to the wild type protein of SEQ ID NO: 1, or which mutant allele has reduced gene expression compared to the wild type allele, b) Analyzing the amount of L-homoserine produced in the leaf tissue of the plants, c) Identifying, and optionally selecting, a plant which comprises in its leaf tissue at least 5.0 nmol of L-homoserine per mg fresh weight of leaf tissue, more preferably at least 6.0, 7.0 or 8.0 nmol L-homoserine per mg fresh weight of leaf tissue, more preferably at least 9.0 nmol or 10.0 nmol or 15.0 nmol or even at least 19 nmol L-homoserine per mg fresh weight of leaf tissue.

In one aspect the plants of a) comprise a wild type HSK allele in homozygous form encoding a homoserine kinase protein of SEQ ID NO: 3 or a protein comprising at least 95% amino acid sequence identity to the protein of SEQ ID NO: 3.

In one aspect the plants of a) comprise SEQ ID NO: 4 in homozygous form.

The method may further comprise determining whether the identified or selected plant of step c) comprises resistance against at least one race of *Bremia lactucae*. Resistance can be tested by various methods, e.g. as described in the Examples or other methods. In one aspect the selected lettuce plant does not produce *Bremia* spores on the leaves, while the same lettuce plant, or another susceptible control lettuce plant, which only contains the wild type HSK allele and produces the wild type HSK protein of SEQ ID NO: 1 (or a variant thereof), does produce *Bremia* spores on the leaves.

Any plant produced by the above method is also an aspect of the invention, as are seeds from which such a plant can be grown.

Also encompassed is a method for detecting whether a lettuce plant or plant part comprises a mutant HSK allele according to the invention. This can be done in various ways. In one aspect it comprises analyzing the DNA for the presence of a mutant allele according to the invention, e.g. by detecting the mutant allele itself (e.g. Single Nucleotide Polymorphism, SNP genotyping, whereby the presence of one or two copies, or the absence of the mutant allele can be detected). The genomic coding sequence which encodes the wild type HSK protein of SEQ ID NO: 1 is provided in SEQ ID NO: 2 herein. Alternatively the presence of a mutant messenger RNA (mRNA) can be detected. The mRNA is identical to the genomic DNA of SEQ ID NO: 2, except that T is replaced by U. Alternatively, the presence of the mutant HSK protein can be detected. Alternatively, a reduced level of expression, e.g. of wild type mRNA (or cDNA) can be detected. In yet another aspect the amount of L-homoserine in the leaf tissue and/or the resistance against *Bremia* can be tested before or after testing whether the plant comprises a mutant HSK allele.

A method for detecting whether a lettuce plant or plant part comprises a mutant HSK allele encoding a protein of SEQ ID NO: 1 which comprises one or more amino acid insertions, deletions or substitutions comprises a) determine the presence in the plant of a mutant nucleic acid molecule comprising one or more nucleotides which are different compared to the genomic DNA of SEQ ID NO: 2 or the mRNA of SEQ ID NO: 2 and whereby the encoded protein comprises one or more amino acids which are different from SEQ ID NO: 1 or which are inserted or deleted compared to SEQ ID NO: 1; or b) determining the presence in the plant of a protein comprising one or more amino acids which are different from the protein of SEQ ID NO: 1 or which are inserted or deleted compared to SEQ ID NO: 1.

In one aspect the mutant nucleic acid molecule encodes a mutant homoserine kinase protein which comprises one or more amino acids, selected from the group consisting of: N64 (Asn at position 64 of SEQ ID NO: 1), D70 (Asp at position 70 of SEQ ID NO: 1), N118 (Asn at position 118 of SEQ ID NO: 1), C119 (Cys at position 119 of SEQ ID NO: 1), K144 (Lys at position 144 of SEQ ID NO: 1), G149 (Gly at position 149 of SEQ ID NO: 1), G151 (Gly at position 151 of SEQ ID NO: 1), L152 (Leu at position 152 of SEQ ID NO: 1), G153 (Gly at position 153 of SEQ ID NO: 1), S154 (Ser at position 154 of SEQ ID NO: 1), S155 (Ser at position 155 of SEQ ID NO: 1), S158 (Ser at position 158 of SEQ ID NO: 1), D196 (Asp at position 196 of SEQ ID NO: 1), N197 (Asn at position 197 of SEQ ID NO: 1), T241 (Thr at position 241 of SEQ ID NO: 1), R245 (Arg at position 245 of SEQ ID NO: 1), R293 (Arg at position 293 of SEQ ID NO: 1) and A320 (Ala at position 320 of SEQ ID NO: 1) being substituted by a different amino acid. In another aspect the mutant nucleic acid molecule encodes a mutant HSK protein in which one or more of the above amino acids are deleted.

In one aspect nucleotide 734 of SEQ ID NO: 2 is changed from a guanine into an adenine, whereby the codon 'agg' (Arginine) is changed into codon 'aag' (Lysine). Thus, in one aspect the nucleic acid molecule comprising an adenine at nucleotide 734 of SEQ ID NO: 2 is detected. For example SNP genotyping can be used to distinguish between the presence of two copies of the wild type allele of SEQ ID NO: 2, one copy of the wild type allele (comprising SEQ ID NO: 2) and one copy of the mutant allele of SEQ ID NO: 2 (comprising an adenine at nucleotide 734 of SEQ ID NO: 2) or two copies of the mutant allele in the genome of the plant or plant part or plant cell.

Thus, in one aspect the lettuce plant of the invention comprises in its genome SEQ ID NO: 2, wherein the codon 733 to 735 (agg) comprises a nucleotide substitution, e.g. nucleotide 734 is changed into a different nucleotide, e.g. adenine. In one aspect a mutation in this codon can be used to detect the mutant allele.

Also provided is a method of growing a plant of the invention in an area where *Bremia lactucae* can occur and harvesting the leaves of the plant.

Likewise the mutant proteins and mutant nucleotide sequences described herein are provided, e.g. in isolated form.

Further, the use of a mutant HSK allele for detecting a lettuce plant or for breeding a lettuce plant which accumulates L-homoserine in the leaf tissue is provided herein.

```
SEQUENCES
HSK protein on chromosome 8
                                               >SEQ ID NO: 1
MAICHHHQPSFTIPSSFPFTTNLSNKSQLHLPSSFRCNLSVTTNLEPEPV

YTAVKSFAPATVANLGPGFDFLGCAVDGIGDYVTLKIDPQVHPGEVSITE

ITGTGNSANKLSKNPIWNCAGIAAISVMKMLNIRSVGLSLSLEKGLPLGS

GLGSSAASAAAAAIAVNEIFGGKLPALDLVLAGLESEAKVSGYHADNIAP

AIMGGFVLVRSYDPLELIPLQFPVDKNLYFVLVNPEFEAPTKKMRAALPK

EITMSHHVWNSSQAGALVAAVLQGDLKGFGKALSSDKIVEPRRAPLIPGM

DAVKKAALEAGAYGCTISGAGPTAVAVTDNEEKGREIGEKMVEAFMAEGN

LKAVAMVKQLDRVGARLVSSISR

genomic DNA, cDNA encoding SEQ ID NO: 1
                                               >SEQ ID NO: 2
ATGGCGATTTGTCATCACCATCAACCTTCATTCACCATCCCTTCTTCTTT

CCCATTCACTACTAATCTTTCAAACAAATCCCAACTTCATCTCCCATCGT

CTTTCCGCTGCAATCTATCCGTCACTACAAATCTCGAACCCGAACCCGTT

TACACCGCCGTCAAGTCATTCGCCCCCGCCACCGTAGCCAACCTCGGCCC

TGGGTTTGACTTTCTCGGTTGCGCAGTCGACGGGATCGGAGACTATGTCA

CCCTCAAAATCGACCCCCAAGTTCACCCTGGCGAGGTCTCAATCACCGAA

ATCACCGGAACCGGCAACTCCGCCAATAAGCTCAGCAAAAACCCTATCTG

GAATTGCGCTGGGATTGCTGCCATTTCTGTCATGAAGATGCTCAACATCC

GATCCGTCGGCCTCTCTCTATCTCTAGAAAAGGGTCTCCCCCTCGGAAGC

GGTCTCGGTTCCAGCGCCGCTAGTGCCGCCGCCGCGGCAATCGCCGTTAA

TGAGATTTTTGGTGGAAAGTTACCTGCATTGGATTTAGTCCTCGCAGGGC
```

-continued

```
TTGAATCGGAAGCTAAAGTATCCGGATACCACGCTGATAACATTGCGCCG

GCAATCATGGGTGGTTTCGTTCTCGTTCGGAGCTACGATCCTTTAGAGCT

GATTCCGTTGCAGTTTCCGGTCGACAAAAACCTCTATTTCGTCTTGGTGA

ATCCGGAATTCGAAGCGCCGACGAAGAAGATGAGGGCGGCGTTACCAAAA

GAGATAACAATGTCGCACCATGTATGGAACAGTAGTCAAGCAGGTGCCTT

GGTGGCGGCGGTGTTGCAGGGGGATTTGAAGGGGTTTGGAAAGGCGTTGT

CTTCTGATAAGATAGTGGAACCGAGGAGGGCGCCATTGATTCCGGGAATG

GATGCTGTGAAGAAGGCTGCACTTGAGGCAGGGGCTTATGGGTGTACGAT

CAGTGGAGCAGGGCCAACTGCGGTGGCTGTTACAGATAACGAGGAAAAAG

GGAGGGAGATTGGGGAGAAGATGGTGGAAGCTTTCATGGCGGAAGGAAAT

TTGAAAGCTGTGGCTATGGTGAAGCAATTGGACAGAGTTGGTGCTAGACT

TGTTAGTAGCATTTCCAGATAA

HSK like protein on chromosome 4
                                               >SEQ ID NO: 3
MAIRHYQPPFASTSSSISSTDLFKPPKLHLSSSVRCNISVASKLEPEPHP

VFTSVKSFAPATVANLGPGFDFLGCAIDGIGDYVTLTVDPQVQPGRLSIA

EINGVDKSSKRLSRNPLWNCAGIAAISVMKMLKIRSVGLSLSINTCLPLR

GGLGSSAASAAAAAVAVNEIFGGKLQDSDLILAGLEAEAKLSGYHADNIA

PAIMGGFVLIRSYDPLELISLKFPPEKNLFFVLVNPEFQAQTKKMRAVLP

TEITMSDHVWNCSQAAALVAGVLQGDLVGFGKALSSDRIVEPRRAPLLPG

MEDVKKAAMEAGAYGCTISGSGPTVVAVTDDEDRGREIGEKMVEAFVEKG

KLKALAMVKKLDRVGARVISRISSQ

genomic DNA, cDNA encoding SEQ ID NO: 3
                                               >SEQ ID NO: 4
ATGGCAATTCGCCATTATCAACCTCCATTCGCCTCCACTTCTTCTTCTAT

CTCTAGTACAGATTTATTCAAACCCCCTAAACTTCATCTTTCATCGTCTG

TCCGGTGCAACATCTCCGTCGCTTCCAAACTGGAACCCGAACCTCATCCA

GTTTTCACCTCCGTTAAGTCATTCGCCCCCGCCACCGTAGCCAACCTCGG

GCCTGGTTTCGACTTCCTCGGCTGCGCAATCGACGGCATCGGAGATTACG

TTACCCTCACAGTCGACCCCCAAGTCCAACCCGGCAGATTATCAATTGCA

GAAATCAACGGCGTTGACAAGTCTTCCAAGAGGCTCAGCAGAAACCCTCT

ATGGAATTGCGCCGGAATTGCTGCAATCTCCGTCATGAAGATGCTCAAGA

TCCGATCCGTTGGCCTCTCTTTATCCATCAATACATGTCTCCCCCTTCGA

GGCGGCCTAGGCTCCAGCGCCGCTAGCGCTGCCGCCGCCGCCGTTGCGGT

TAATGAGATTTTCGGAGGGAAGTTACAGGATTCCGATTTGATACTCGCGG

GGCTCGAAGCTGAAGCGAAGTTATCCGGTTATCACGCCGATAACATTGCT

CCGGCGATCATGGGCGGGTTTGTGTTGATCAGAAGCTACGATCCATTAGA

GTTGATCTCCTTGAAGTTTCCACCGGAAAAGAATCTGTTTTTCGTGTTGG

TGAATCCTGAATTCCAAGCACAAACGAAGAAGATGAGGGCGGTTCTACCG

ACGGAGATAACAATGTCGGATCATGTATGGAATTGTAGTCAGGCGGCAGC

GTTGGTGGCAGGCGTATTGCAGGGGGATTTGGTGGGGTTTGGGAAGGCAT

TGTCATCGGATAGAATTGTGGAGCCACGGCGGGCGCCATTGCTTCCGGGG
```

-continued

ATGGAAGATGTGAAGAAGGCAGCAATGGAAGCAGGGGCATATGGGTGTAC

GATAAGTGGGTCAGGGCCGACGGTGGTGGCGGTGACGGATGATGAAGATA

GAGGGAGGGAGATCGGGGAGAAGATGGTGGAAGCTTTTGTGGAGAAGGGA

AAGTTGAAAGCTTTGGCTATGGTGAAGAAACTGGACAGAGTTGGTGCTAG

AGTTATCAGTCGTATCTCCAGCCAATGA

EXAMPLES

Identification of HSK-Like Genes in Lettuce

To identify the lettuce orthologs of the *Arabidopsis* DMR1 gene, the *Arabidopsis* DMR1 (Homoserine Kinase, HSK) protein sequence (At2g17265) was aligned (tblastn alignment) to the translated lettuce genome V8 using the blast tool on the Lettuce Genome Research website of UCDavis Genome Centre. This led to the identification of two lettuce genes with amino acid sequence identity to the *Arabidopsis* protein. See Table 1 in the specification.

Based on the homology of both proteins to the *Arabidopsis* HSK gene, both proteins are considered to be HSK-like proteins. Since in *Arabidopsis* HSK is encoded by only one gene, the presence of two genes in lettuce was surprising and therefore we analyzed gene expression to determine whether both genes are active.

Gene Expression of the HSK-Like Genes in Lettuce

Expression was determined by analyzing RNA seq reads from Next Gen Seq sequence analyses from NCBI databases in an in-house Genome browser (JBrowse). In general, the number of reads, used as a measure for gene activity, is comparable for both genes in leaves of lettuce. This strongly suggests that both HSK-like genes are translated into mRNA and may therefore contribute to the HSK-activity in leaves. Therefore, we decided to screen for mutations in both genes to determine whether mutations in either one of the genes or in both genes can lead to increased homoserine level and *Bremia lactucae* resistance.

Generation of EMS Mutants and Screening of Mutants in Lettuce HSK-Like Genes

Lettuce mutants were generated by incubating lettuce seeds in a solution of EMS in water for several hours. After washing with water, the seeds were sown in soil and allowed to flower and self pollinate to set M2 seed (Mutant 2$^{nd}$ generation seed). M2 seeds were collected per plant and a small fraction of the seeds were used for DNA isolation. The DNA representing M2 seeds families was used to amplify fragments of the homoserine kinase-like genes. These PCR fragments were sequenced to identify possible mutations. The identified mutations were evaluated using SIFT analysis (Sorting Intolerant From Tolerant) which is a program that predicts whether an amino acid substitution may affect protein function so that users can prioritize substitutions for further study.

The mutants were tested for *Bremia* resistance and in parallel the homoserine level was measured twice in young leaves. See below.

Homoserine Measurements

Amino Acid Extraction

Leaf tissue was frozen in liquid nitrogen and ground in Eppendorf tubes using Eppendorf micropestles. Aliquots of 10-50 mg fresh weight (FW) were taken in new Eppendorf tubes and weighed. Amino acids were extracted with 750 μl 80% ethanol (twice), supernatants were pooled in a new tube. Amino acid extracts were lyophilized using a freeze dryer and dissolved in 150 μl 80% ethanol. Additional aliquots of 10-50 mg FW were taken and dried o/n at 95° C. to determine the FW/DW ratio per sample.

Amino Acid Detection

An EZfaast kit (Phenomenex) was used to clean-up and derivatize concentrated amino acid extracts, according to the manufacturer's instructions. Shortly, this includes adding 100 μl 0.2 mM Norvaline as an internal standard to each of the samples, solid phase extraction using a cation-exchange resin filled sorbent tip, derivatization producing chloroformate derivatives of amino and carboxylic acid groups and lastly liquid-liquid extraction using a combination of organic solvents. The supplied Amino Acid Standard mixture was mixed in a 1:1 ratio with 200 nmol/mL solution of L-Homoserine (Sigma-Aldrich). To create an amino acid calibration curve, 25 μl, 50 μl 100 μl and 200 μl of the obtained amino acid standard mixture including homoserine was extracted and derivatized using the EZfaast kit as described above. Amino acids were separated by gas chromatography—flame ionization detection (GC-FID) on an Agilent Technologies 7890A GC system, using an Agilent Technologies 7683B series injector. A Phenomenex ZB-AAA, 10 m×250 μm Zebron Amino Acid column was used on the GC-FID system. Parameters for GC-FID are as described in the EZfaast kit manual.

Amino Acid Quantification

Amino Acid peaks were called based on retention time, using Agilent Chemstation software. Total peak areas per amino acid per sample were normalized using the peak are of the internal standard (Norvaline). Calibration curves were constructed based on the normalized peak areas of the amino acid mixture, measured in four concentrations as described above. Obtained calibration curves were used to calculate the amino acid amounts in the samples in nmol.

TABLE A-1

Homoserine measurements for plants comprising mutations in HSK gene encoding SEQ ID NO: 1 (experiment 1)

| Plant | Amino Acid substitution in SEQ ID NO: 1 | SIFT prediction on protein activity | Zygosity of mutant allele | Homoserine levels in nmol per mg Fresh Weight (nmol/mgFW) | Homoserine levels in nmol per mg Dry Weight (nmol/mgDW) | *Bremia* resistance Bl: 25 (see tests below) |
|---|---|---|---|---|---|---|
| CERVINO_M-312H2 | V233M | Not tolerated | Heterozygous | 0.00 | 0.0 | No data |
| CERVINO_M-312H2 | V233M | Not tolerated | Homozygous | 0.00 | 0.0 | No data |
| WENDEL_M-1418H1 | P223L | Not tolerated | Homozygous | 0.00 | 0.0 | No |
| WENDEL_M-1418H1 | P223L | Not tolerated | Homozygous | 0.00 | 0.0 | No |
| WENDEL_M-1503H1 | E238K | Not tolerated | Heterozygous | 0.00 | 0.0 | No |
| WENDEL_M-1503H1 | E238K | Not tolerated | Homozygous | 0.38 | 6.4 | No |
| WENDEL_M-1848H1 | R245K | Not tolerated | Heterozygous | 0.00 | 0.0 | No |
| WENDEL_M-1848H1 | R245K | Not tolerated | Homozygous | 19.46 | 302.3 | Yes |
| Cervino | Wild type | | | 0.00 | 0.0 | No |
| Wendel | Wild type | | | 0.00 | 0.0 | No |

TABLE A-1-continued

| Homoserine measurements for plants comprising mutations in HSK gene encoding SEQ ID NO: 1 (experiment 1) | | | | | | |
|---|---|---|---|---|---|---|
| Plant | Amino Acid substitution in SEQ ID NO: 1 | SIFT prediction on protein activity | Zygosity of mutant allele | Homoserine levels in nmol per mg Fresh Weight (nmol/mgFW) | Homoserine levels in nmol per mg Dry Weight (nmol/mgDW) | *Bremia* resistance Bl: 25 (see tests below) |
| *Bremia* susceptible control | Wild type | | | 0.00 | 0.0 | No |
| *Bremia* resistant control | Wild type | | | 0.00 | 0.0 | yes |

TABLE A-2

| Homoserine measurements for plants comprising mutations in HSK gene encoding SEQ ID NO: 1 (experiment 2) | | | | | |
|---|---|---|---|---|---|
| Plant | Amino Acid substitution in SEQ ID NO: 1 | SIFT prediction on protein activity | Zygosity of mutant allele | Homoserine levels in nmol per mg Fresh Weight (nmol/mgFW) | *Bremia* resistance Bl: 26 (data not shown) |
| WENDEL_M-1108H2 | M244I | tolerated | Homozygous | 4.41 | No |
| WENDEL_M-589H2 | P219S | tolerated | homozygous | −0.01 | No |
| Cervino | Wild type | | | 0.00 | No |
| Wendel | Wild type | | | 0.00 | No |

From the above it is clear that mutations in the HSK gene encoding SEQ ID NO: 1 only lead to *Bremia* resistance if a minimal amount of L-homoserine accumulates in the leaves, as the mutants having an amount of 4.41 nmol/mg FW, or less, did not result in *Bremia* resistance, while the mutant having an amount of 19.46 nmol/mgFW of L-homoserine in the leaves was resistant against *Bremia lactucae*.

TABLE B-1

| Homoserine measurements for plants comprising mutations in HSK gene encoding SEQ ID NO: 3 (experiment 1) | | | | | | |
|---|---|---|---|---|---|---|
| Plant | Amino Acid substitution in SEQ ID NO: 3 | SIFT prediction on protein activity | Zygosity of mutant allele | Homoserine levels in nmol per mg Fresh Weight (nmol/mgFW) | Homoserine levels in nmol per mg Dry Weight (nmol/mgDW) | *Bremia* resistance Bl: 25 (see tests below) |
| CERVINO_M-712H1 | D82N | Not tolerated | Homozygous | 0.00 | 0.0 | No |
| CERVINO_M-712H1 | D82N | Not tolerated | Homozygous | 0.00 | 0.0 | No |
| CERVINO_M-748H2 | V278M | Not tolerated | Homozygous | −0.01 | −0.1 | No |
| CERVINO_M-748H2 | V278M | Not tolerated | Homozygous | 0.00 | 0.0 | No |
| CERVINO_M-787H2 | P292S | Not tolerated | Homozygous | 0.00 | 0.0 | No |
| CERVINO_M-787H2 | P292S | Not tolerated | Homozygous | 0.00 | 0.0 | No |
| CERVINO_M-863H1 | G104D | Not tolerated | Homozygous | 0.00 | 0.0 | No |
| CERVINO_M-863H1 | G104D | Not tolerated | Homozygous | 0.00 | 0.0 | No |
| CERVINO_M-972H2 | P250L | Not tolerated | Homozygous | 0.00 | 0.0 | No |
| CERVINO_M-972H2 | P250L | Not tolerated | Homozygous | 0.00 | 0.0 | No |
| CERVINO_M-1049H2 | S127F | Not tolerated | Heterozygous | 0.00 | 0.0 | No |
| CERVINO_M-1049H2 | S127F | Not tolerated | Homozygous | 0.00 | 0.0 | No |
| CERVINO_M-1473H1 | V278M | Not tolerated | Homozygous | 0.00 | 0.0 | No |
| CERVINO_M-1473H1 | V278M | Not tolerated | Homozygous | 0.00 | 0.0 | No |
| WENDEL_M-195H2 | P236S | Not tolerated | Homozygous | −0.01 | −0.1 | No |
| WENDEL_M-195H2 | P236S | Not tolerated | Homozygous | 0.00 | 0.0 | No |
| WENDEL_M-518H1 | G81R | Tolerated | Homozygous | 0.00 | 0.0 | No |
| WENDEL_M-518H1 | G81R | Tolerated | Homozygous | 0.00 | 0.0 | No |
| WENDEL_M-1121H1 | T62I | Not tolerated | Homozygous | 0.00 | −0.1 | No |
| WENDEL_M-1121H1 | T62I | Not tolerated | Homozygous | 0.00 | 0.0 | No |
| WENDEL_M-1121H2 | T62I | Not tolerated | Homozygous | 0.00 | 0.0 | No |
| WENDEL_M-1121H2 | T62I | Not tolerated | Homozygous | 0.00 | 0.0 | No |
| Cervino | Wild type | | | 0.00 | 0.0 | No |
| Wendel | Wild type | | | 0.00 | 0.0 | No |
| *Bremia* susceptible control | Wild type | | | 0.00 | 0.0 | No |
| *Bremia* resistant control | Wild type | | | 0.00 | 0.0 | yes |

TABLE B-2

Homoserine measurements for plants comprising mutations in HSK gene encoding SEQ ID NO: 3 (experiment 2)

| Plant | Amino Acid substitution in SEQ ID NO: 3 | SIFT prediction on protein activity | Zygosity of mutant allele | Homoserine levels in nmol per mg Fresh Weight (nmol/mgFW) | *Bremia* resistance Bl: 21 (data not shown) | *Bremia* resistance Bl: 26 (data not shown) |
|---|---|---|---|---|---|---|
| CERVINO_M-1049H2 | S127F | Not tolerated | homozygous | 0.00 | No | No |
| CERVINO_M-611H2 | C262Y | tolerated | homozygous | −0.01 | No | No |
| CERVINO_M-1H2 | P116S | tolerated | homozygous | −0.01 | No | No |
| CERVINO_M-726H2 | P68S | tolerated | homozygous | 0.00 | No | No |
| CERVINO_M-732H2 | G122R | tolerated | homozygous | 0.0 | No | No |
| CERVINO_M-1595H1 | C75Y | tolerated | homozygous | 0.0 | No | No |
| Cervino | Wild type | | | 0.00 | No | No |
| Wendel | Wild type | | | 0.00 | Yes* | No |

*Wendel contains the resistance gene R18 conferring resistance against Bl: 1-16, 19, 21, 23 and 32EU.

From the above it can be seen that none of the mutations in the gene encoding SEQ ID NO: 3 result in an increase in L-homoserine.

*Bremia lactucae* Resistance Test—"Leaf Disk Test" (LDT)

Material and Solutions

Blotting paper: 255×435 mm (original size); Grade 358, 135 g/m$^2$; Munktell & Filtrak GmbH, Germany.

Black plastic boxes: 460×310×80 mm.

Plastic bags: LPDE transparent bags; 400×600 mm; 0.05 mm thickness; Paardekooper Verpakkingen B.V., Netherlands.

Plastic jars: Straight sample container with screw cap (PS clear); 33×70 mm (int.Ø×h); 60 ml capacity; VWR, Netherlands.

Cheese cloth: Cotton cheesecloth; C. van't Riet Zuiveltechnologie, Netherlands.

Spraying equipment: 1 liter mechanical pump sprayer with maximum operating pressure of 3 bar (Gloria type 89 Profiline; GLORIA Haus-und Gartengeräte GmbH, Germany) fitted with a brass spray lance/extension and nozzle (GLORIA Haus-und Gartengeräte GmbH, Germany).

Nutrient Solution: The Nutrient Solution consists of 1× Hoagland No 2 basal salt mixture supplemented with 50 mg/L Iprodione. The Nutrient Solution is prepared by re-suspending 1.63 g of Hoagland's No 2 basal salt mixture (See Appendix 02 for exact composition) (Caisson Labs, US) and 10 ml of 5 g/L Iprodione laboratory stock into 1 L of tap water. The Nutrient Solution is made the same morning as the leaf disk test will be inoculated.

APPENDIX 02

Ingredients Hoagland's No2 Basal salt mixture.

| Components | mg/L |
|---|---|
| Ammonium Phosphate, Monobasic (NH4H2PO4) | 115.03 |
| Boric Acid (H3BO3) | 2.86 |
| Calcium Nitrate, Tetrahydrate (Ca(NO3)2•4H2O) | 656.40 |
| Cupric Sulfate, Pentahydrate (CuSO4•5H2O) | 0.08 |
| Ferric Tartrate (C12Fe2H12O8) | 5.32 |
| Magnesium Sulfate, Anhydrous (MgSO4) | 240.76 |
| Manganese Chloride, Tetrahydrate (MnCl2•4H2O) | 1.81 |
| Molybdenum Trioxide (MoO3) | 0.02 |
| Potassium Nitrate (KNO3) | 606.60 |
| Zinc Nitrate, Hexahydrate (Zn(NO3)2•6H2O) | 0.22 |

Trial Design

Seeds are sown on Day 1 (See Appendix 01 for planning). Material to be tested will be sown together with plants that are known to be resistant or susceptible for the isolates that are used in the test.

The disease test is performed on healthy looking 4 weeks old plants in the 6$^{th}$ to 8$^{th}$ leaf stage.

Plants that do not look healthy are discarded.

For each pathogen race/plant combination, at least two leaf disks are tested in separate boxes. In total, a minimum of 4 leaf disks are tested per plant.

In each black box, one leaf disk is placed per plant in the grid drawn on the blotting paper. The grid will be filled with leaf disks corresponding with the printed grid. Among the leaf disks in a box there will be leaf disks of the susceptible and resistant control plants at fixed positions.

For example in the test with race BI:25EU, the resistant control used was variety Balesta, and the susceptible control used was variety Cervino and/or Wendel. In the test with race BI: 26EU, NunDM17 was used as resistant control and Cervino and/or Wendel as susceptible control. In the test with race BI:21 Cervino was used as susceptible control, while Wendel and/or NunDm17 were used as resistant varieties. Other varieties with known resistance or susceptibility to *Bremia* races can be equally used, such as those described in the UPOV test guidelines for lettuce, on the world wide web at uov.int/edocs/tgdocs/en/tg013.pdf.

APPENDIX 01

*B. lactucae* leaf disk test experiment planning.

| Week | Day post inoculation | Event |
|---|---|---|
| 1 | 1 | Sowing of plants to test |
| 4 | 28 | (i) Inoculum preparation |
| | | (ii) Inoculation of leaf disks |
| 6 | 39 | Intermediate scoring (11 dpi) |
| 6 | 42 | Final scoring (14 dpi) |

Preparing Inoculum

The preparation of *B. lactucae* inocula needed for the trial inoculation begins on Day 28. Make sure to wear gloves whenever handling *B. lactucae*. The preparation goes as follow:

The plastic jar containing the relevant *B. lactucae* working stocks is taken out of the −20° C. freezer and approximately 50 ml of cold tap water is added to the jar (the jar is left standing for a while after this step). Make sure the water is cold by having the tap open for a while before taking any water. The jar is vigorously shaken a few times to loosen the spores into the water. A workable size is cut off a "cheese cloth" using scissors. The content of the jar is then filtered through a layer of wet-made "cheese cloth", into a clean measuring cup (usually size 200 ml). Squeeze the cloth after you have softly poured the content of the jar onto the cheese cloth.

The spore concentration of the inoculum is measured using a hemocytometer (Bürker Türk). Where necessary, the spore concentration is adjusted to reach $1\times10^5$ spores $ml^{-1}$. Note that in cases where the concentration is too low, the content of an additional jar of working stock should be used to reach the desired concentration.

Once prepared, the spore solution is dispensed into a 1 liter mechanical pump sprayer. Two jars of working stock is usually enough to prepare a spore solution for inoculating 6 boxes of leaf disks.

Trial Inoculation

Three sheets of blotting papers are stacked on top of each other. The top sheet has either several lines drawn on it using a ruler and a pencil to form a grid used to designate the position of the leaf disks or a printed grid. The stack of blotting papers are placed at the bottom of a black plastic box.

The stack of blotting papers is humidified using the Nutrient Solution (see above).

One or two leaves are removed from each plant to be tested. Leaf disks of 17 mm in diameter are punched out of the leaves. The leaf punch is laid upside down on the top sheet of blotting paper in the square that corresponds with the printed lay-out and a record is made when the actual lay-out differs from the printed lay-out (e.g. plant is not available).

When all leaf disks are in place, the prepared inoculum solution is sprayed evenly over the leaf discs to the point of solution "run off".

Following inoculation, the black boxes are placed inside clear plastic bags (bags are closed with pegs). From that point on, the boxes will remain inside closed bags throughout the test (except of course for scorings).

The bagged boxes are moved to the climate cells (12/12 hours day/night cycle using standard fluorescent light bulbs; light intensity is 70 μmol/$m^2$/s (PAR); temperature is 15° C. constant. Daylight period is from 20.00 μm until 08.00 am. Directly after inoculation a dark period of approximately 24 hours is applied by covering the inoculated trays with thick light impermeable sheets. The boxes are kept in the climate cells until the end of the experiment.

Data Collection and Analysis

For each test, two scorings are done. An intermediate scoring is done at 11 dpi (days post inoculation). A final scoring is done at 14 dpi. At each time point two scores are taken: a) the percentage of leaf disc surface area displaying *Bremia lactucae* sporulation, on a scale of 0% to 100% and b) the intensity/severity of the sporulation on the surface area which displays spores. The intensity/severity is scored on a scale of 0-100 (the score given is the average severity of the area with sporulation).

Results:

The Tables below show the results of resistance tests using *Bremia lactucae* strain BI:25EU (European strain). The TILLING populations used do not contain resistance against this race. Only the results of the final scoring are shown.

In one aspect a plant is considered resistant against a *Bremia* race, such as BI:25EU, when the score is 0% sporulation. The resistant control should have a score of 0% sporulation. The susceptible control should have a score of 100% sporulation.

TABLE A

Resistance of mutants comprising an amino acid substitution in SEQ ID NO: 1

| Plant | Amino Acid substitution in SEQ ID NO: 1 | Zygosity of mutant allele | % surface area showing sporulating (0-100%) Repetition 1 | Intensity of sporulation on surface area (scale 0-100) Repetition 1 | % surface area showing sporulating (0-100%) Repetition 2 | Intensity of sporulation on surface area (scale 0-100) Repetition 2 | Overall Conclusion S = susceptible R = resistant |
|---|---|---|---|---|---|---|---|
| Susceptible control | | susceptible | 100 | 100 | 100 | 100 | S |
| Susceptible control | | susceptible | 100 | 100 | 100 | 100 | S |
| Resistant control | | resistant | 0 | 0 | 0 | 0 | R |
| Susceptible control | | susceptible | 100 | 100 | 100 | 100 | S |
| WENDEL_M-1418H1 | P223L | Heterozygous | 100 | 100 | 80 | 100 | S |
| WENDEL_M-1418H1 | P223L | Homozygous | 100 | 100 | 100 | 100 | |
| WENDEL_M-1418H1 | P223L | Homozygous | 75 | 100 | 100 | 100 | |
| WENDEL_M-1418H1 | P223L | Homozygous | 80 | 100 | 100 | 100 | |
| WENDEL_M-1503H1 | E238K | Heterozygous | 100 | 100 | 100 | 100 | S |
| WENDEL_M-1503H1 | E238K | Heterozygous | 100 | 100 | 100 | 100 | |
| WENDEL_M-1503H1 | E238K | Heterozygous | 50 | 100 | 100 | 100 | |
| WENDEL_M-1503H1 | E238K | Heterozygous | 100 | 100 | 100 | 100 | |
| WENDEL_M-1503H1 | E238K | Homozygous | 100 | 100 | 100 | 100 | |
| WENDEL_M-1848H1 | R245K | Heterozygous | 100 | 100 | 80 | 100 | S |
| WENDEL_M-1848H1 | R245K | Homozygous | 0 | 0 | | | R |
| Susceptible control | | susceptible | 100 | 100 | 100 | 100 | S |
| Resistant control | | resistant | 0 | 0 | 0 | 0 | R |
| Resistant control | | resistant | 0 | 0 | 0 | 0 | R |
| Susceptible control | | susceptible | 100 | 100 | 100 | 100 | S |

For empty datapoints, no data were available

TABLE B

Resistance of mutants comprising an amino acid substitution in SEQ ID NO: 3

| Plant | Amino Acid substitution in SEQ ID NO: 3 | Zygosity of mutant allele | % surface area showing sporulating (0-100%) Repetition 1 | Intensity of sporulation on surface area (scale 0-100) Repetition 1 | % surface area showing sporulating (0-100%) Repetition 2 | Intensity of sporulation on surface area (scale 0-100) Repetition 2 | Overall Conclusion for plant genotype S = susceptible R = resistant |
|---|---|---|---|---|---|---|---|
| Susceptible control | | | 100 | 100 | 100 | 100 | S |
| Resistant control | | | 0 | 0 | 0 | 0 | R |
| CERVINO_M-712H1 | D82N | Homozygous | 80 | 100 | 50 | 100 | S |
| CERVINO_M-712H1 | D82N | Homozygous | 75 | 100 | 100 | 100 | |
| CERVINO_M-712H1 | D82N | Homozygous | 70 | 100 | 100 | 75 | |
| CERVINO_M-712H1 | D82N | Homozygous | 100 | 75 | 75 | 100 | |
| CERVINO_M-712H1 | D82N | Homozygous | 75 | 100 | 90 | 100 | |
| CERVINO_M-748H2 | V278M | Heterozygous | | | 100 | 100 | S |
| CERVINO_M-748H2 | V278M | Homozygous | 100 | 100 | 100 | 100 | |
| CERVINO_M-748H2 | V278M | Homozygous | 80 | 100 | 100 | 75 | |
| CERVINO_M-748H2 | V278M | Homozygous | 100 | 100 | 80 | 100 | |
| CERVINO_M-748H2 | V278M | Homozygous | 100 | 100 | 100 | 100 | |
| CERVINO_M-787H2 | P292S | Heterozygous | 100 | 100 | 80 | 100 | S |
| CERVINO_M-787H2 | P292S | Heterozygous | 75 | 75 | 100 | 75 | |
| CERVINO_M-787H2 | P292S | Homozygous | 75 | 100 | 100 | 100 | |
| CERVINO_M-787H2 | P292S | Homozygous | 75 | 100 | 75 | 75 | |
| CERVINO_M-787H2 | P292S | Homozygous | 90 | 100 | 100 | 100 | |
| Susceptible control | | susceptible | 100 | 100 | 100 | 100 | S |
| CERVINO_M-863H1 | G104D | Homozygous | 100 | 75 | 40 | 100 | S |
| CERVINO_M-863H1 | G104D | Homozygous | 50 | 100 | 100 | 100 | |
| CERVINO_M-863H1 | G104D | Homozygous | 50 | 100 | 75 | 100 | |
| CERVINO_M-863H1 | G104D | Homozygous | | | 75 | 100 | |
| CERVINO_M-863H1 | G104D | Homozygous | 80 | 75 | 75 | 50 | |
| CERVINO_M-972H2 | P250L | Homozygous | 90 | 100 | 100 | 100 | S |
| CERVINO_M-972H2 | P250L | Homozygous | 100 | 100 | 75 | 100 | |
| CERVINO_M-972H2 | P250L | Homozygous | 100 | 100 | 75 | 100 | |
| CERVINO_M-972H2 | P250L | Homozygous | 10 | 25 | 100 | 75 | |
| CERVINO_M-972H2 | P250L | Homozygous | 100 | 100 | 100 | 100 | |
| CERVINO_M-972H2 | P250L | Heterozygous | 60 | 100 | 50 | 100 | |
| Susceptible control | | susceptible | 100 | 100 | 100 | 100 | S |
| CERVINO_M-1049H2 | S127F | Heterozygous | 100 | 75 | 100 | 100 | S |
| CERVINO_M-1049H2 | S127F | Heterozygous | 100 | 100 | 75 | 75 | |
| CERVINO_M-1049H2 | S127F | Homozygous | 50 | 100 | 25 | 75 | |
| CERVINO_M-972H2 | P250L | Heterozygous | 25 | 75 | 100 | 100 | S |
| CERVINO_M-972H2 | P250L | Heterozygous | 80 | 100 | 50 | 100 | |
| Resistant control | | resistant | 0 | 0 | 0 | 0 | R |
| Susceptible control | | susceptible | 100 | 100 | 100 | 100 | S |
| Susceptible control | | susceptible | 100 | 100 | 100 | 100 | S |
| Resistant control | | resistant | 0 | 0 | 0 | 0 | R |
| Resistant control | | resistant | 0 | 0 | 0 | 0 | R |
| Susceptible control | | susceptible | 100 | 100 | 100 | 100 | S |
| CERVINO_M-1473H1 | V278M | Homozygous | 100 | 100 | 10 | 100 | S |
| CERVINO_M-1473H1 | V278M | Homozygous | 100 | 100 | 100 | 75 | |
| CERVINO_M-1473H1 | V278M | Homozygous | 100 | 100 | 100 | 100 | |
| CERVINO_M-1473H1 | V278M | Homozygous | 80 | 100 | 50 | 75 | |
| CERVINO_M-1473H1 | V278M | Homozygous | 100 | 75 | 100 | 100 | |
| WENDEL_M-195H2 | P236S | Homozygous | 100 | 100 | 100 | 100 | S |
| WENDEL_M-195H2 | P236S | Heterozygous | 100 | 100 | 100 | 100 | |
| WENDEL_M-195H2 | P236S | Heterozygous | 50 | 100 | 50 | 100 | |
| WENDEL_M-195H2 | P236S | Heterozygous | 100 | 100 | 100 | 100 | |
| WENDEL_M-195H2 | P236S | Homozygous | 100 | 100 | 100 | 100 | |
| Susceptible control | | susceptible | 100 | 100 | 100 | 100 | S |
| WENDEL_M-518H1 | G81R | Heterozygous | 100 | 100 | 100 | 100 | S |
| WENDEL_M-518H1 | G81R | Heterozygous | 100 | 100 | | | |
| WENDEL_M-518H1 | G81R | Homozygous | 100 | 100 | 100 | 100 | |
| WENDEL_M-518H1 | G81R | Homozygous | 100 | 100 | 100 | 100 | |
| WENDEL_M-518H1 | G81R | Homozygous | 100 | 100 | 100 | 100 | |
| WENDEL_M-1121H1 | T62I | Heterozygous | 100 | 100 | 100 | 100 | S |
| WENDEL_M-1121H1 | T62I | Heterozygous | 100 | 100 | 100 | 100 | |
| WENDEL_M-1121H1 | T62I | Heterozygous | 100 | 100 | 50 | 100 | |
| WENDEL_M-1121H1 | T62I | Homozygous | 100 | 100 | 100 | 100 | |
| WENDEL_M-1121H1 | T62I | Homozygous | 100 | 100 | 100 | 100 | |
| WENDEL_M-1121H1 | T62I | Homozygous | 100 | 100 | 100 | 75 | |
| WENDEL_M-1121H1 | T62I | Homozygous | 25 | 100 | 100 | 100 | |
| WENDEL_M-1121H1 | T62I | Homozygous | 100 | 100 | 100 | 100 | |
| WENDEL_M-1121H2 | T62I | Heterozygous | 100 | 100 | 100 | 100 | |
| WENDEL_M-1121H2 | T62I | Homozygous | 100 | 100 | 100 | 100 | |
| WENDEL_M-1121H2 | T62I | Heterozygous | 100 | 100 | 100 | 50 | |
| WENDEL_M-1121H2 | T62I | Homozygous | 100 | 100 | 100 | 100 | |
| WENDEL_M-1121H2 | T62I | Homozygous | 80 | 100 | 100 | 100 | |

TABLE B-continued

| Resistance of mutants comprising an amino acid substitution in SEQ ID NO: 3 | | | | | | | |
|---|---|---|---|---|---|---|---|
| Plant | Amino Acid substitution in SEQ ID NO: 3 | Zygosity of mutant allele | % surface area showing sporulating (0-100%) Repetition 1 | Intensity of sporulation on surface area (scale 0-100) Repetition 1 | % surface area showing sporulating (0-100%) Repetition 2 | Intensity of sporulation on surface area (scale 0-100) Repetition 2 | Overall Conclusion for plant genotype S = susceptible R = resistant |
| Susceptible control | | susceptible | 100 | 100 | 100 | 100 | S |
| Resistant control | | resistant | 0 | 0 | 0 | 0 | R |

For empty datapoints, no data were available

Three-Dimensional Structure Analysis of the HSK Proteins

In order to find out why amino acid R245 of SEQ ID NO: 1 led to such a high accumulation of L-homoserine in planta, while the other mutants did not, the *Arabidopsis* HSK amino acid sequence was BLASTed against the PDB database (Protein Data Bank). This identified the Crystal structure of the homoserine kinase protein 1H72 (PDB ID 1H72). Alignment of the *Arabidopsis* HSK protein with the HSK Crystal structure (PDB ID 1H72, Crystal structure of Homoserine Kinase complexed with homoserine) lead to the identification of 18 amino acid residues, which interact with L-homoserine or with ATP (Adenosine tri-phosphate), as shown in FIG. 2. These 18 amino acids were then also identified in the lettuce protein of SEQ ID NO: 1. The finding that R245 was one of the 18 amino acids which interact with homoserine or ATP in the wild type protein of SEQ ID NO: 1 explained why the substitution of this amino acid resulted in a lower phosphorylation of homoserine and thus to an accumulation of L-homoserine.

The invention claimed is:

1. A cultivated plant of the species *Lactuca sativa* which is homozygous for a mutant allele of the wild type homoserine kinase gene encoding SEQ ID NO: 1, wherein the mutant allele encodes a mutant homoserine kinase protein comprising one or more amino acids being substituted by a different amino acid compared to the wild type protein of SEQ ID NO: 1 resulting in the leaf tissue of said lettuce plant accumulating L-homoserine, while a plant heterozygous for the mutant allele or lacking the mutant allele does not comprise L-homoserine in the leaf tissue; wherein said L-homoserine in the leaf tissue confers resistance against *Bremia lactucae*, and wherein the one or more amino acids are selected from the group consisting of N64 (Asn at position 64 of SEQ ID NO: 1), D70 (Asp at position 70 of SEQ ID NO: 1), N118 (Asn at position 118 of SEQ ID NO: 1), C119 (Cys at position 119 of SEQ ID NO: 1), K144 (Lys at position 144 of SEQ ID NO: 1), G149 (Gly at position 149 of SEQ ID NO: 1), G151 (Gly at position 151 of SEQ ID NO: 1), L152 (Leu at position 152 of SEQ ID NO: 1), G153 (Gly at position 153 of SEQ ID NO: 1), S154 (Ser at position 154 of SEQ ID NO: 1), S155 (Ser at position 155 of SEQ ID NO: 1), S158 (Ser at position 158 of SEQ ID NO: 1), D196 (Asp at position 196 of SEQ ID NO: 1), N197 (Asn at position 197 of SEQ ID NO: 1), T24 (Thr at position 241 of SEQ ID NO: 1), R245 (Arg at position 245 of SEQ ID NO: 1), R293 (Arg at position 293 of SEQ ID NO: 1), A320 (Ala at position 320 of SEQ ID NO: 1), and M244 (Met at position 244 of SEQ ID NO: 1).

2. The plant according to claim 1, wherein the plant is homozygous for the wild type allele of the homoserine kinase gene encoding the homoserine kinase protein of SEQ ID NO: 3.

3. The plant according to claim 1, wherein the mutant allele encodes a mutant homoserine kinase protein which comprises the amino acid Arginine (Arg, R) at amino acid number 245 of SEQ ID NO: 1 being replaced by a different amino acid.

4. The plant according to claim 3, wherein the leaf tissue comprises an amount of L-homoserine of at least 15.0 nmol per mg fresh weight.

5. The plant according to claim 1, wherein the amount of said L-homoserine in the leaf tissue is high enough to prevent sporulation of *Bremia lactucae* under conditions where the susceptible control plant shows 100% sporulation.

6. A seed from which a plant according to claim 1 can be grown.

7. A lettuce leaf or lettuce head of a plant grown from the seed of claim 6; wherein the lettuce leaf or the lettuce head comprises the mutant allele and the L-homoserine.

8. The plant according to claim 3, wherein the different amino acid is Lysine (Lys, K).

9. A method of producing a lettuce plant comprising crossing the plant of claim 1 with a lettuce plant, and obtaining seeds from the crossing.

10. The method of claim 9, further comprising growing the seeds.

11. The plant according to claim 1, wherein the mutant allele encodes a mutant homoserine kinase protein which comprises the amino acid Methionine (M, Met) at amino acid number 244 of SEQ ID NO: 1 being replaced by a different amino acid.

12. The plant according to claim 11, wherein the different amino acid is Isoleucine (Ile, I).

13. The plant according to claim 1, wherein the mutant allele encodes a mutant homoserine kinase protein which comprises the amino acid Arginine (Arg, R) at amino acid number 245 of SEQ ID NO: 1 being replaced by a Lysine (Lys, K), and the amino acid Methionine (M, Met) at amino acid number 244 of SEQ ID NO: 1 being replaced by a Isoleucine (Ile, I).

* * * * *

```
                         SEQUENCE LISTING


<160> NUMBER OF SEQ ID NOS: 4

<210> SEQ ID NO 1
<211> LENGTH: 373
<212> TYPE: PRT
<213> ORGANISM: Lactuca sativa

<400> SEQUENCE: 1

Met Ala Ile Cys His His His Gln Pro Ser Phe Thr Ile Pro Ser Ser
1               5                   10                  15

Phe Pro Phe Thr Thr Asn Leu Ser Asn Lys Ser Gln Leu His Leu Pro
            20                  25                  30

Ser Ser Phe Arg Cys Asn Leu Ser Val Thr Thr Asn Leu Glu Pro Glu
        35                  40                  45

Pro Val Tyr Thr Ala Val Lys Ser Phe Ala Pro Ala Thr Val Ala Asn
    50                  55                  60

Leu Gly Pro Gly Phe Asp Phe Leu Gly Cys Ala Val Asp Gly Ile Gly
65                  70                  75                  80

Asp Tyr Val Thr Leu Lys Ile Asp Pro Gln Val His Pro Gly Glu Val
                85                  90                  95

Ser Ile Thr Glu Ile Thr Gly Thr Gly Asn Ser Ala Asn Lys Leu Ser
            100                 105                 110

Lys Asn Pro Ile Trp Asn Cys Ala Gly Ile Ala Ala Ile Ser Val Met
        115                 120                 125

Lys Met Leu Asn Ile Arg Ser Val Gly Leu Ser Leu Ser Leu Glu Lys
    130                 135                 140

Gly Leu Pro Leu Gly Ser Gly Leu Gly Ser Ser Ala Ala Ser Ala Ala
145                 150                 155                 160

Ala Ala Ala Ile Ala Val Asn Glu Ile Phe Gly Gly Lys Leu Pro Ala
                165                 170                 175

Leu Asp Leu Val Leu Ala Gly Leu Glu Ser Glu Ala Lys Val Ser Gly
            180                 185                 190

Tyr His Ala Asp Asn Ile Ala Pro Ala Ile Met Gly Gly Phe Val Leu
        195                 200                 205

Val Arg Ser Tyr Asp Pro Leu Glu Leu Ile Pro Leu Gln Phe Pro Val
```

-continued

```
    210                 215                 220

Asp Lys Asn Leu Tyr Phe Val Leu Val Asn Pro Glu Phe Glu Ala Pro
225                 230                 235                 240

Thr Lys Lys Met Arg Ala Ala Leu Pro Lys Glu Ile Thr Met Ser His
                245                 250                 255

His Val Trp Asn Ser Ser Gln Ala Gly Ala Leu Val Ala Ala Val Leu
            260                 265                 270

Gln Gly Asp Leu Lys Gly Phe Gly Lys Ala Leu Ser Ser Asp Lys Ile
        275                 280                 285

Val Glu Pro Arg Arg Ala Pro Leu Ile Pro Gly Met Asp Ala Val Lys
    290                 295                 300

Lys Ala Ala Leu Glu Ala Gly Ala Tyr Gly Cys Thr Ile Ser Gly Ala
305                 310                 315                 320

Gly Pro Thr Ala Val Ala Val Thr Asp Asn Glu Glu Lys Gly Arg Glu
                325                 330                 335

Ile Gly Glu Lys Met Val Glu Ala Phe Met Ala Glu Gly Asn Leu Lys
            340                 345                 350

Ala Val Ala Met Val Lys Gln Leu Asp Arg Val Gly Ala Arg Leu Val
        355                 360                 365

Ser Ser Ile Ser Arg
    370


<210> SEQ ID NO 2
<211> LENGTH: 1122
<212> TYPE: DNA
<213> ORGANISM: Lactuca sativa

<400> SEQUENCE: 2

atggcgattt gtcatcacca tcaaccttca ttcaccatcc cttcttcttt cccattcact     60

actaatcttt caaacaaatc ccaacttcat ctcccatcgt ctttccgctg caatctatcc    120

gtcactacaa atctcgaacc cgaacccgtt tacaccgccg tcaagtcatt cgccccccgcc    180

accgtagcca acctcggccc tgggtttgac tttctcggtt gcgcagtcga cgggatcgga    240

gactatgtca ccctcaaaat cgacccccaa gttcaccctg gcgaggtctc aatcaccgaa    300

atcaccggaa ccggcaactc cgccaataag ctcagcaaaa accctatctg gaattgcgct    360

gggattgctg ccatttctgt catgaagatg ctcaacatcc gatccgtcgg cctctctcta    420

tctctagaaa agggtctccc cctcggaagc ggtctcggtt ccagcgccgc tagtgccgcc    480

gccgcggcaa tcgccgttaa tgagattttt ggtggaaagt tacctgcatt ggatttagtc    540

ctcgcagggc ttgaatcgga agctaaagta tccggatacc acgctgataa cattgcgccg    600

gcaatcatgg gtggtttcgt tctcgttcgg agctacgatc ctttagagct gattccgttg    660

cagtttccgg tcgacaaaaa cctctatttc gtcttggtga atccggaatt cgaagcgccg    720

acgaagaaga tgagggcggc gttaccaaaa gagataacaa tgtcgcacca tgtatggaac    780

agtagtcaag caggtgcctt ggtggcggcg gtgttgcagg gggatttgaa ggggtttgga    840

aaggcgttgt cttctgataa gatagtggaa ccgaggaggg cgccattgat tccgggaatg    900

gatgctgtga agaaggctgc acttgaggca ggggcttatg ggtgtacgat cagtggagca    960

gggccaactg cggtggctgt tacagataac gaggaaaaag ggagggagat tggggagaag   1020

atggtggaag ctttcatggc ggaaggaaat ttgaaagctg tggctatggt gaagcaattg   1080

gacagagttg gtgctagact tgttagtagc atttccagat aa                      1122
```

<210> SEQ ID NO 3
<211> LENGTH: 375
<212> TYPE: PRT
<213> ORGANISM: lactuca sativa

<400> SEQUENCE: 3

```
Met Ala Ile Arg His Tyr Gln Pro Pro Phe Ala Ser Thr Ser Ser Ser
1               5                   10                  15

Ile Ser Ser Thr Asp Leu Phe Lys Pro Pro Lys Leu His Leu Ser Ser
            20                  25                  30

Ser Val Arg Cys Asn Ile Ser Val Ala Ser Lys Leu Glu Pro Glu Pro
        35                  40                  45

His Pro Val Phe Thr Ser Val Lys Ser Phe Ala Pro Ala Thr Val Ala
    50                  55                  60

Asn Leu Gly Pro Gly Phe Asp Phe Leu Gly Cys Ala Ile Asp Gly Ile
65                  70                  75                  80

Gly Asp Tyr Val Thr Leu Thr Val Asp Pro Gln Val Gln Pro Gly Arg
                85                  90                  95

Leu Ser Ile Ala Glu Ile Asn Gly Val Asp Lys Ser Ser Lys Arg Leu
            100                 105                 110

Ser Arg Asn Pro Leu Trp Asn Cys Ala Gly Ile Ala Ala Ile Ser Val
        115                 120                 125

Met Lys Met Leu Lys Ile Arg Ser Val Gly Leu Ser Leu Ser Ile Asn
    130                 135                 140

Thr Cys Leu Pro Leu Arg Gly Gly Leu Gly Ser Ser Ala Ala Ser Ala
145                 150                 155                 160

Ala Ala Ala Ala Val Ala Val Asn Glu Ile Phe Gly Gly Lys Leu Gln
                165                 170                 175

Asp Ser Asp Leu Ile Leu Ala Gly Leu Glu Ala Glu Ala Lys Leu Ser
            180                 185                 190

Gly Tyr His Ala Asp Asn Ile Ala Pro Ala Ile Met Gly Gly Phe Val
        195                 200                 205

Leu Ile Arg Ser Tyr Asp Pro Leu Glu Leu Ile Ser Leu Lys Phe Pro
    210                 215                 220

Pro Glu Lys Asn Leu Phe Phe Val Leu Val Asn Pro Glu Phe Gln Ala
225                 230                 235                 240

Gln Thr Lys Lys Met Arg Ala Val Leu Pro Thr Glu Ile Thr Met Ser
                245                 250                 255

Asp His Val Trp Asn Cys Ser Gln Ala Ala Ala Leu Val Ala Gly Val
            260                 265                 270

Leu Gln Gly Asp Leu Val Gly Phe Gly Lys Ala Leu Ser Ser Asp Arg
        275                 280                 285

Ile Val Glu Pro Arg Arg Ala Pro Leu Leu Pro Gly Met Glu Asp Val
    290                 295                 300

Lys Lys Ala Ala Met Glu Ala Gly Ala Tyr Gly Cys Thr Ile Ser Gly
305                 310                 315                 320

Ser Gly Pro Thr Val Val Ala Val Thr Asp Asp Glu Asp Arg Gly Arg
                325                 330                 335

Glu Ile Gly Glu Lys Met Val Glu Ala Phe Val Glu Lys Gly Lys Leu
            340                 345                 350

Lys Ala Leu Ala Met Val Lys Lys Leu Asp Arg Val Gly Ala Arg Val
        355                 360                 365

Ile Ser Arg Ile Ser Ser Gln
    370                 375
```

-continued

```
<210> SEQ ID NO 4
<211> LENGTH: 1128
<212> TYPE: DNA
<213> ORGANISM: lactuca sativa

<400> SEQUENCE: 4

atggcaattc gccattatca acctccattc gcctccactt cttcttctat ctctagtaca      60

gatttattca aaccccctaa acttcatctt tcatcgtctg tccggtgcaa catctccgtc     120

gcttccaaac tggaacccga acctcatcca gttttcacct ccgttaagtc attcgccccc     180

gccaccgtag ccaacctcgg gcctggtttc gacttcctcg gctgcgcaat cgacggcatc     240

ggagattacg ttaccctcac agtcgacccc caagtccaac ccggcagatt atcaattgca     300

gaaatcaacg gcgttgacaa gtcttccaag aggctcagca gaaaccctct atggaattgc     360

gccggaattg ctgcaatctc cgtcatgaag atgctcaaga tccgatccgt tggcctctct     420

ttatccatca atacatgtct ccccccttcga ggcggcctag gctccagcgc cgctagcgct     480

gccgccgccg ccgttgcggt taatgagatt ttcggaggga agttacagga ttccgatttg     540

atactcgcgg ggctcgaagc tgaagcgaag ttatccggtt atcacgccga taacattgct     600

ccggcgatca tgggcgggtt tgtgttgatc agaagctacg atccattaga gttgatctcc     660

ttgaagtttc caccggaaaa gaatctgttt ttcgtgttgg tgaatcctga attccaagca     720

caaacgaaga agatgagggc ggttctaccg acggagataa caatgtcgga tcatgtatgg     780

aattgtagtc aggcggcagc gttggtggca ggcgtattgc agggggattt ggtggggttt     840

gggaaggcat tgtcatcgga tagaattgtg gagccacggc gggcgccatt gcttccgggg     900

atggaagatg tgaagaaggc agcaatggaa gcaggggcat atgggtgtac gataagtggg     960

tcagggccga cggtggtggc ggtgacggat gatgaagata gagggaggga gatcggggag    1020

aagatggtgg aagcttttgt ggagaaggga aagttgaaag ctttggctat ggtgaagaaa    1080

ctggacagag ttggtgctag agttatcagt cgtatctcca gccaatga                 1128
```